United States Patent
Podrebarac et al.

(10) Patent No.: US 12,227,466 B2
(45) Date of Patent: Feb. 18, 2025

(54) METHODS AND SYSTEMS FOR PERFORMING OXIDATIVE COUPLING OF METHANE

(71) Applicant: Lummus Technology LLC, Houston, TX (US)

(72) Inventors: Gary Podrebarac, Friendswood, TX (US); Zan Liu, Katy, TX (US); Khalid Azzam, Sugarland, TX (US); Daniel Rosenberg, Dunaujvaros (HU)

(73) Assignee: Lummus Technology LLC, Houston, TX (US)

( * ) Notice: Subject to any disclaimer, the term of this patent is extended or adjusted under 35 U.S.C. 154(b) by 150 days.

(21) Appl. No.: 17/898,715

(22) Filed: Aug. 30, 2022

(65) Prior Publication Data
US 2023/0061675 A1 Mar. 2, 2023

Related U.S. Application Data

(60) Provisional application No. 63/238,816, filed on Aug. 31, 2021.

(51) Int. Cl.
*C07C 2/84* (2006.01)

(52) U.S. Cl.
CPC .......... *C07C 2/84* (2013.01); *C07C 2523/26* (2013.01); *C07C 2523/42* (2013.01); *C07C 2523/72* (2013.01)

(58) Field of Classification Search
None
See application file for complete search history.

(56) References Cited

U.S. PATENT DOCUMENTS

| 2,324,172 A | 7/1943 | Parkhurst |
| 2,486,980 A | 11/1949 | Robinson |

(Continued)

FOREIGN PATENT DOCUMENTS

| CA | 2041874 C | 4/1999 |
| CA | 2765769 A1 | 1/2011 |

(Continued)

OTHER PUBLICATIONS

Agarwal, et al., Aqueous Au—Pd colloids catalyze selective CH4 oxidation to CH3OH with O2 under mild conditions, Science 358, Oct. 13, 2017, 223-27.

(Continued)

*Primary Examiner* — Ali Z Fadhel
(74) *Attorney, Agent, or Firm* — Calfee, Halter & Griswold LLP

(57) ABSTRACT

A method of performing an oxidative coupling of methane (OCM) reaction to produce $C_{2+}$ compounds using a low temperature gas mixture feed is provided. The method includes introducing a gas mixture feed containing methane, oxygen, hydrogen, and carbon monoxide at a temperature of less than or equal to 300° C. to an inlet of an OCM reactor, which contains a combustion catalyst and an OCM catalyst. At least a portion of the gas mixture feed is combusted using the combustion catalyst to generate a heated gas mixture having a temperature of at least 450° C. The heated gas mixture contacts the OCM catalyst to initiate an OCM reaction and produce an OCM effluent that includes $C_{2+}$ compounds. A system for performing an OCM reaction using a low temperature feedstock gas mixture is also provided.

23 Claims, 6 Drawing Sheets

(56) References Cited

U.S. PATENT DOCUMENTS

| | | |
|---|---|---|
| 2,577,701 A | 12/1951 | Philip et al. |
| 2,579,601 A | 12/1951 | Nelson et al. |
| 2,621,216 A | 12/1952 | White |
| 2,643,216 A | 6/1953 | Findlay |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hagemeyer, Jr. et al. |
| 3,516,262 A | 6/1970 | Bernstein |
| 3,584,071 A | 6/1971 | McNulty et al. |
| 3,596,473 A | 8/1971 | Streich |
| 3,660,519 A | 5/1972 | Takaaki et al. |
| 3,686,334 A | 8/1972 | Britton |
| 3,686,350 A | 8/1972 | Ono et al. |
| 3,702,886 A | 11/1972 | Argauer et al. |
| 3,706,534 A | 12/1972 | Verheul et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Hutson et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,115,086 A | 9/1978 | Jordan et al. |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,418,045 A | 11/1983 | Sato et al. |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,519,824 A | 5/1985 | Huebel |
| 4,523,049 A | 6/1985 | Jones et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,889,545 A | 12/1989 | Campbell et al. |
| 4,891,457 A | 1/1990 | Owen et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,026,934 A | 6/1991 | Bains et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,095,161 A | 3/1992 | Abrevaya et al. |
| 5,113,032 A | 5/1992 | Cameron et al. |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,245,099 A | 9/1993 | Mitariten |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,457,256 A | 10/1995 | Mitariten et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Eyshon |
| RE35,633 E | 10/1997 | Leyshon |
| 5,679,241 A | 10/1997 | Stanley et al. |

(56) References Cited

U.S. PATENT DOCUMENTS

| | | |
|---|---|---|
| 5,702,589 A | 12/1997 | Tsang et al. |
| 5,712,217 A | 1/1998 | Choudhary et al. |
| 5,714,657 A | 2/1998 | deVries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Peter et al. |
| 5,935,898 A | 8/1999 | Peter et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,342,149 B1 | 1/2002 | Koester et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,602,920 B2 | 8/2003 | Hall et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,793,517 B2 | 9/2010 | Patel et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,080,697 B2 | 12/2011 | Lin et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |

(56) References Cited

U.S. PATENT DOCUMENTS

| | | |
|---|---|---|
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Attner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild Hansen |
| 8,912,109 B2 | 12/2014 | Chinta et al. |
| 8,912,381 B2 | 12/2014 | Chinta et al. |
| 8,921,256 B2 | 12/2014 | Ras et al. |
| 8,962,517 B2 | 2/2015 | Merzlyak et al. |
| 8,993,473 B2 | 3/2015 | Melde et al. |
| 9,040,762 B2 | 5/2015 | Ras et al. |
| 9,079,815 B2 | 7/2015 | Mukherjee et al. |
| 9,133,079 B2 | 9/2015 | Weinberger et al. |
| 9,180,426 B2 | 11/2015 | Pawlak et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,126,071 B2 | 11/2018 | Wortmann et al. |
| 10,183,900 B2 | 1/2019 | Nyce et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 | 9/2019 | Radaelli et al. |
| 10,787,398 B2 | 9/2020 | Nyce et al. |
| 10,787,400 B2 | 9/2020 | Radaelli et al. |
| 10,793,490 B2 | 10/2020 | Radaelli et al. |
| 10,829,424 B2 | 11/2020 | Rafique et al. |
| 10,836,689 B2 | 11/2020 | Cizeron et al. |
| 10,843,982 B2 | 11/2020 | Sarsani et al. |
| 10,858,247 B2 | 12/2020 | Finnerty et al. |
| 10,865,165 B2 | 12/2020 | Nyce et al. |
| 10,870,611 B2 | 12/2020 | Radaelli et al. |
| 10,894,751 B2 | 1/2021 | Nyce et al. |
| 10,927,056 B2 | 2/2021 | Cizeron et al. |
| 10,941,088 B1 | 3/2021 | Sarsani et al. |
| 10,960,343 B2 | 3/2021 | Jonnavittula et al. |
| 10,995,044 B2 | 5/2021 | Sarsani et al. |
| 11,001,542 B2 | 5/2021 | McCormick et al. |
| 11,001,543 B2 | 5/2021 | Duggal et al. |
| 11,008,265 B2 | 5/2021 | Rafique et al. |
| 11,168,038 B2 | 11/2021 | Nyce et al. |
| 11,186,529 B2 | 11/2021 | Duggal et al. |
| 11,208,364 B2 | 12/2021 | Rafique et al. |
| 11,242,298 B2 | 2/2022 | Iyer et al. |
| 11,254,626 B2 | 2/2022 | Weinberger et al. |
| 11,254,627 B2 | 2/2022 | Nyce et al. |
| 11,407,695 B2 | 8/2022 | Cizeron et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0021379 A1 | 2/2006 | Ronczy |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith, Jr. et al. |
| 2006/0283780 A1 | 12/2006 | Spivey et al. |
| 2007/0027030 A1 | 2/2007 | Cheung et al. |
| 2007/0073083 A1* | 3/2007 | Sunley .................. C07C 2/84 562/519 |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1 | 6/2008 | Bozzano et al. |
| 2008/0194900 A1 | 8/2008 | Bhirud |
| 2008/0207975 A1 | 8/2008 | Crone et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0105066 A1 | 4/2009 | Kang et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2009/0312591 A1 | 12/2009 | Schubert et al. |
| 2010/0000153 A1 | 1/2010 | Kurkjian et al. |

(56) References Cited

U.S. PATENT DOCUMENTS

| | | |
|---|---|---|
| 2010/0003179 A1 | 1/2010 | Katusic et al. |
| 2010/0028735 A1 | 2/2010 | Basset et al. |
| 2010/0059216 A1 | 3/2010 | Bruckmann et al. |
| 2010/0140144 A1 | 6/2010 | Clinton et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |
| 2010/0256245 A1 | 10/2010 | Taccino et al. |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2012/0302807 A1 | 11/2012 | Elseviers |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0246856 A1 | 9/2015 | Schmigalle et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0145170 A1 | 5/2016 | Keusenkothen et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Zhang et al. |
| 2016/0376148 A1 | 12/2016 | Mamedov et al. |
| 2017/0014807 A1 | 1/2017 | Liang et al. |
| 2017/0022125 A1 | 1/2017 | Fichtl |
| 2017/0057889 A1 | 3/2017 | Sarsani et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0062642 A1 | 2/2019 | Nei et al. |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |
| 2020/0031734 A1 | 1/2020 | Cizeron et al. |
| 2020/0031736 A1 | 1/2020 | Weinberger et al. |
| 2020/0048165 A1 | 2/2020 | Duggal et al. |
| 2020/0054983 A1 | 2/2020 | Jonnavittula et al. |
| 2020/0055796 A1 | 2/2020 | Nyce et al. |
| 2020/0071242 A1 | 3/2020 | Patel et al. |

(56) References Cited

U.S. PATENT DOCUMENTS

| | | |
|---|---|---|
| 2020/0131100 A1 | 4/2020 | Schammel et al. |
| 2020/0172452 A1 | 6/2020 | Duggal et al. |
| 2020/0189994 A1 | 6/2020 | Radaelli et al. |
| 2020/0207684 A1 | 7/2020 | Rafique et al. |
| 2020/0207685 A1 | 7/2020 | Nyce et al. |
| 2020/0216370 A1 | 7/2020 | Rafique et al. |
| 2020/0231519 A1 | 7/2020 | Abudawoud et al. |

FOREIGN PATENT DOCUMENTS

| | | |
|---|---|---|
| CA | 2800142 C | 6/2018 |
| CN | 1403375 A | 3/2003 |
| CN | 1432550 A | 7/2003 |
| CN | 101224432 A | 7/2008 |
| CN | 101387019 A | 3/2009 |
| CN | 101747927 A | 6/2010 |
| CN | 102093157 A | 6/2011 |
| CN | 102125825 A | 7/2011 |
| CN | 102950017 A | 3/2013 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 253522 A2 | 1/1988 |
| EP | 303438 A2 | 2/1989 |
| EP | 336823 A1 | 10/1989 |
| EP | 608447 A1 | 8/1994 |
| EP | 634211 A1 | 1/1995 |
| EP | 722822 A1 | 7/1996 |
| EP | 761307 A1 | 3/1997 |
| EP | 764467 A1 | 3/1997 |
| EP | 716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 1231437 A | 5/1971 |
| GB | 2191212 A | 12/1987 |
| JP | 2005161225 A | 6/2005 |
| RU | 2412147 C2 | 2/2011 |
| RU | 2435830 C1 | 12/2011 |
| RU | 2447048 C1 | 4/2012 |
| WO | 8607351 A1 | 12/1986 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 A2 | 7/2005 |
| WO | 2007125360 A1 | 11/2007 |
| WO | 2007130515 A2 | 11/2007 |
| WO | 2008005055 A2 | 1/2008 |
| WO | 2008014081 A1 | 2/2008 |
| WO | 2008022147 A1 | 2/2008 |
| WO | 2008073143 A2 | 6/2008 |
| WO | 2008150451 A2 | 12/2008 |
| WO | 2008150451 A3 | 3/2009 |
| WO | 2009071463 A2 | 6/2009 |
| WO | 2009074203 A1 | 6/2009 |
| WO | 2009115805 A1 | 9/2009 |
| WO | 2010005453 A2 | 1/2010 |
| WO | 2011008464 A1 | 1/2011 |
| WO | 2011041184 A2 | 4/2011 |
| WO | 2011050359 A1 | 4/2011 |
| WO | 2010069488 A8 | 5/2011 |
| WO | 2011104328 A2 | 9/2011 |
| WO | 2011149996 A2 | 12/2011 |
| WO | 2012047274 A2 | 4/2012 |
| WO | 2012047274 A3 | 5/2012 |
| WO | 2012162526 A2 | 11/2012 |
| WO | 2013106771 A2 | 7/2013 |
| WO | 2013169462 A1 | 11/2013 |
| WO | 2013175204 A1 | 11/2013 |
| WO | 2013177433 A2 | 11/2013 |
| WO | 2013177461 A2 | 11/2013 |
| WO | 2014011646 A1 | 1/2014 |
| WO | 2014044387 A1 | 3/2014 |
| WO | 2014049445 A2 | 4/2014 |
| WO | 2014089479 A1 | 6/2014 |
| WO | 2013177433 A3 | 8/2014 |
| WO | 2014131435 A1 | 9/2014 |
| WO | 2014143880 A1 | 9/2014 |
| WO | 2015000061 A1 | 1/2015 |
| WO | 2015003193 A1 | 1/2015 |
| WO | 2015021177 A1 | 2/2015 |
| WO | 2015048295 A1 | 4/2015 |
| WO | 2015066693 A1 | 5/2015 |
| WO | 2015081122 A2 | 6/2015 |
| WO | 2015105911 A1 | 7/2015 |
| WO | 2015106023 A1 | 7/2015 |
| WO | 2015081122 A3 | 12/2015 |
| WO | 2016012371 A1 | 1/2016 |
| WO | 2016149507 A1 | 9/2016 |
| WO | 2016160563 A1 | 10/2016 |
| WO | 2016205411 A2 | 12/2016 |
| WO | 2016210006 A2 | 12/2016 |
| WO | 2016210006 A3 | 4/2017 |
| WO | 2017065947 A1 | 4/2017 |
| WO | 2016205411 A3 | 9/2017 |
| WO | 2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | 2018118105 A1 | 6/2018 |
| WO | 2019010498 A1 | 1/2019 |
| WO | 2019055220 A1 | 3/2019 |
| WO | 2021066285 A1 | 4/2021 |

OTHER PUBLICATIONS

Ahari, et al. Effects of operating parameters on oxidative coupling of methane over Na—WMn/SiO2 catalyst at elevated pressures. Journal of Natural Gas Chemistry. vol. 20, Issue 2, Mar. 2011, pp. 204-213.

American Petroleum Institute Publication 534 Heat Recovery Steam Generators Jan. 1995 (51 pages).

Autothermal Partial Oxidative Coupling of Methane. IP.com, Prior Art Database Technical Disclosure, Jul. 29, 2008, 5 pages.

Barrett, et al. The determination of pore vol. and area distributions in porous substances—Computations from nitrogen isotherms. J. Am. Chem. Soc., 1951, vol. 73, pp. 373-380.

Berstad, D. et al. Low-temperature CO2 removal from natural gas. Energy Procedia (2012) 26:41-48.

Bloch, et al. Hydrocarbon Separations in a Metal-Organic Framework with Open Iron(II) Coordination Sites, Science, 2012, 335:1606-1610.

Bollmann, et al. Ethylene tetramerization: a new route to produce 1-octene in exceptionally high selectivities. J Am Chem Soc. Nov. 17, 2004;126(45):14712-3.

Botella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.

Carter, et al. High activity ethylene trimerisation catalysts based on diphosphine ligands. Chem Commun (Camb). Apr. 21, 2002;(8):858-9.

Caskey, et al., Dramatic Tuning of Carbon Dioxide Uptake via Metal Substitution in a Coordination Polymer with Cylindrical Pores, J. Am. Chem. Soc., (2009), 130(33): 10870-71.

Cavani, et al. Oxidative dehydrogenation of ethane and propane: How far from commercial implementation? Catalysis Today. 2007; 127(1-4):113-131.

(56) References Cited

OTHER PUBLICATIONS

Chemsystems PERP Report Ethylene Oxide/Ethylene Glycol 2005.
Chen, et al. M2 Forming—A Process for Aromatization of Light Hydrocarbons. Ind. Eng. Chem. Process. Des. Dev. 1986, 25, 151-155.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): 15-25, Feb. 2004.
Choudhary, et al. Surface Basicity and Acidity of Alkaline Earth-Promoted La2 03 Catalysts and Their Performance In Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
International Search Report and Written Opinion dated Dec. 15, 2022 for PCT/US2022/041972.
Corma, From Microporous to Mesoporous Molecular Sieve Materials and Their Use in Catalysis, Chem. Rev., 97, 1997, pp. 2373-2419.
Debart, et al. α-MNO2 Nanowires: A catalyst for the O2 Electrode in Rechargeable Lithium Batteries. Angewandte Chemie International Edition 47: 4521-4524, 2008.
Dietzel, et al., Adsorption properties and structure of CO2 adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009) 18:156-160.
Duan, et al. Three-dimensional copper (II) metal-organic framework with open metal sites and anthracene nucleus for highly selective C2H2/CH4 and C2NH2/CO2 gas separation at room temperature. Microporous and Mesoporous Materials. vol. 181, Nov. 15, 2013, pp. 99-104.
Sugiura, Kei et al., "Low-temperature catalytic oxidative coupling of methane in an electric field over aCe-W-O catalyst system", Scientific Reports, Apr. 27, 2016 (Publication date), vol. 6, Article No. 25154, Internal pp. 1-9.
Enger, et al. A review of catalytic partial oxidation of methane to synthesis gas with emphasis on reaction mechanisms over transition metal catalysts. Applied Catalysis A: General 346 (1-2): 1-27, Aug. 2008.
Fallah, et al., A New Nano-(2Li2O/MgO) Catalyst/Porous Alpha-Alumina Composite for the Oxidative Coupling of Methane Reaction, AlChE Journal, Mar. 2010, 56(3):717-28.
Gao, et al. A study on methanol steam reforming to CO2 and H2 over the La2 CO4 nanofiber catalyst. Journal of Solid State Chemistry 181: 7-13, 2008.
Gao, et al. The direct decomposition of NO over the La2 CuO4 nanofiber catalyst. Journal of Solid State Chemistry 181: 2804-2807, 2008.
Geier, et al., Selective adsorption of ethylene over ethane and propylene over propane in the metal-organic frameworks M2(dobdc) (M = Mg, Mn, Fe, Co, Ni, Zn), Chem. Sci., 2013, 4:2054-2061.
Ghosh, et al., Absorption of carbon dioxide into aqueous potassium carbonate promoted by boric acid, Energy Procedia, Feb. 2009, pp. 1075-1081.
Godini, et al. Techno-economic analysis of integrating the methane oxidative coupling and methane reforming processes. Fuel processing technology 2013 v.106 pp. 684-694.
Goto et al., Mesoporous Material from Zeolite, Journal of Poruous Materials, 2002, pp. 43-48.
Graves, C.R. Recycling CO2 into Sustainable Hydrocarbon Fuels: Electrolysis of CO2 and H2O. Dissertation, Columbia University (2010).
Guo, et al. Current Status and Some Perspectives of Rare Earth Catalytic Materials. Journal of The Chinese Rare Earth Society 25(1): 1-15, Feb. 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4(4):128-131.
Haag, W.O. et al. Aromatics, Light Olefins and Gasoline from Methanol: Mechanistic Pathways with ZSM-5 Zeolite Catalyst. J Mol Catalysis (1982) 17:161-169.
He, et al. A microporus metal-organic framework for highly selective separation of acetylene, ethylene, and ethane from methane at room temperature. Chemistry. Jan. 9, 2012; 18(2):613-9. doi 10.1002/chem.201102734. Epub Dec. 8, 2011.
Hosseinpour, Performance of CaX Zeolite for Separation of C2H6, C2H4, and CH4 by Adsorption Process; Capacity, Selectivity, and Dynamic Adsorption Measurements, Separation Science and Technology, 2011, 46:349-355.
Huang, et al. Exploiting shape effects of La2O3 nanocrystals for oxidative coupling of methane reaction. Nanoscale 5(22): 10844-10848, 2013.
Huang, et al. Exploiting shape effects of La2O3 nanocrystals for oxidative coupling of methane reaction. Nanoscale—Electronic Supplementary Material, 2013, 7 pages.
Iwamoto, M. One step formation of propene from ethene or ethanol through metathesis on nickel ion-loaded silica. Molecules. Sep. 13, 2011;16(9):7844-63.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, Gas-Adsorption Processes: State of the Art, American Chemical Society, 1983,pp. 145-169.
Keller, et al. Synthesis of Ethylene via Oxidative Coupling of Methane. Journal of Catalysis 73: 9-19, 1982.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078- 4080, 2008.
Wang, et al. Low temperature selective oxidation of methane to ethane and ethylene over BaCO3/La2 O3 catalysts prepared by urea combustion method. Catalysis communications 7: 5963, 2006.
Wang, et al., Critical Influence of BaCO3 on Low Temperature Catalytic Activity of BaCO3/ZrO2 Catalysts for Oxidative Coupling of Methane, Catalysis Letters (2009), 129:156-162.
Water Electrolysis & Renewable Energy Systems. FuelCellToday (May 2013).
Wikipedia search, Adiabatic Process, Mar. 2011, 10 pages.
Witek-Krowiak, A. et al. Carbon Dioxide Removal in a Membrane Contactor-Selection of Absorptive Liquid/Membrane System. Intl J Chem Eng and Appl. (2012) 3(6):391-395.
Wong, et al. Oxidative coupling of methane over alkali metal oxide promoted La2 O3/BaCO3 catalysts. J. Chem. Tech. Biotechnol. 65:351-354, 1996.
Wu, et al., High-Capacity Methane Storage in Metal-Organic Frameworks M2(dhtp): The Important Role of Open Metal Sites, J. Am. Chem. Soc. 131 (13):4995-5000, Mar. 10, 2009.
Xu, et al. Maximise ethylene gain and acetylene selective hydrogenation efficiency. Petroleum technology quarterly 18.3 (2013): 39-42.
Xu, G et al. An Improved CO2 Separation and Purification System Based on Cryogenic Separation and Distillation Theory. Energies (2014) 7:3484-3502.
Yan, D. Modeling and Application of a Thermoelectric Generator. Thesis, Univ. Toronto (2011).
Yang, et al. Anistropic synthesis of boat shaped core shell Au—Ag nanocrystals and nanowires. Nanotechnology 17:2304-2310, 2006.

(56) References Cited

OTHER PUBLICATIONS

Yu, et al. Oxidative coupling of methane over acceptor-doped SrTi O3: Correlation between p- type conductivity and C2 selectivity and C2 yield. Journal of Catalysis. 13 (5): 338-344, 1992.
Zhang, Q. Journal of Natural Gas Chem., 12:81, 2003.
Zhao, et al. Technologies and catalysts for catalytic preparation of ethene. Industrial catalysis 12 (Supplement):285-289, 2004.
Zhou, et al. Functionalization of lanthanum hydroxide nanowires by atom transfer radical polymerization. Nanotechnology 18, 2007, 7 pages.
Zhou. BP-UOP Cyclar Process. Handbook of Petroleum Refining Processes, The McGraw-Hill Companies (2004), pp. 2.29-2.38.
Zhou, et al., Enhanced H2 Adsorption in Isostructural Metal-Organic Frameworks with Open Metal Sites: Strong Dependence of the Binding Strength on Metal lons, J. Am. Chem. Soc., 2008, 130(46):15268-69.
Zimmerman, et al. Ethylene. Ulmann's Encyclopedia of Industrial Chemistry, Wiley-VCH Verlag Gmbh & Co. KGaA, Weinheim, Germany, 2009, 66 pages.
Chemical Engineering—"Separation Processes: Supercritical CO2: A Green Solvent" Feb. 1, 2010.
Labinger. Oxidative coupling of methane: an inherent limit to selectivity? Catal. Lett. 1988; 1:371-376.
Li, B. et al. Advances in CO2 capture technology: A patent review. Applied Energy (2013) 102:1439-1447.
Li, et al. Combined Single-Pass Conversion of Methane via Oxidative Coupling and Dehydroaromatization. Catalysis Letters, Sep. 2003, vol. 89, Issue 3-4, pp. 275-279.
Li, et al. "Gasoline-Range Hydrocarbon Synthesis over Cobalt-Based Fischer-Tropsch Catalysts Supported on SIO2/HZDM-5," Energy and Fuels. 2008, 22: 1897-1901.
Ling, et al. Preparation of Ag core Au shell Nanowires and Their Surface Enhanced Raman Spectroscopic Studies. Acta Chimica Sinica. 65 (9): 779-784, 2007.
Liu, et al. A novel Na2 W04-Mn.SiC monolithic foam catalyst with improved thermal properties for the oxidative coupling of methane. Catalysis Communications 9: 1302-1306, 2008.
Liu, et al. Increasing the Density of Adsorbed Hydrogen with Coordinatively Unsaturated Metal Centers in Metal-Organic Frameworks Langmuir, 2008, 24:4772-77.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Lunsford, et al. The oxidative coupling of methane on chlorinated Lithium-doped magnesium oxide. J. Chem. Soc., Chem. Commun., 1991, 1430-1432.
Makal, et al., Methane storage in advanced porous materials, Critical Review, Chem. Soc. Rev., 2012, 41 :7761-7779.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Mokhatab et al. "Handbook of Natural Gas Transmission and Processing: Principles and Practices" 2015. Chapter 7, pp. 237-242. (Year: 2015).
Morgan, C.R. et al. Gasoline from Alcohols. Ind Eng Chem Prod Res Dev(1981) 20:185-190.
Natural Gas Spec Sheet, 2003, prepared by Florida Power and Light Company.

Neltner, et al. Production of Hydrogen Using Nanocrystalline Protein-templated catalysts on M12 Phage. ACSNano 1(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Niu, et al. Preparation and characterization of La2 O3CO3 nanowires with high surface areas. Journal of the Chinese Rare Earth Society 23 (Spec. Issue): 33-36, Dec. 2005.
Ogura et al. Formation of Uniform Mesopores in ZSM-5 Zeolite through Treatment in Alkaline Solution, Chemistry Letters, 2000, pp. 882-883.
Ohashi, Y et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Olefins Conversion Technology, Website Accessed Aug. 28, 2014, http:www.CBI.com.
Pak, et al. Elementary Reactions in the Oxidative Coupling of Methane over Mn/NA2 WO4/SiO2 and MN/NA2 WO4/MgO Catalysts. Journal of Catalysis 179:222-230, 1998.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37): 10275-7. doi: 10.1039/c1cc14051e. Epub Aug. 2, 20112.
Process Systems; "Steam Tables" Apr. 8, 2017—https://web.archive.org/web/20170408152403/https://valvesonline.com.au/references/steamtables/.
Qiu, et al. Steady-state conversion of methane to aromatics in high yields using an integrated recycle reaction system. Catalysis Letters 48: 11-15, 1997.
Rousseau, Handbook of Separation Process Technology, 1987, p. 682.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK—Conference, Hamburg, Germany (2007).
Simons, K. Membrane Technologies for CO2 Capture. Dissertation, U. of Twente (2010).
Smith, et al. Recent developments in solvent absorption technologies at the CO2CRC in Australia. Energy Procedia 1(2009): 1549-1555.
Somorjai, et al. High technology catalysts towards 100% selectivity Fabrication, characterization and reaction studies. Catalysis today 100:201-215, 2005.
Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Tabak, S.A. et al. Conversion of Methanol over ZSM-5 to Fuels and Chemicals. Cat Today (1990) 307-327.
Takanabe, et al. Mechanistic Aspects and Reaction Pathways for Oxidative Coupling of Methane on Mn/NA2 WO4/SiO2 Catalysts. Journal of Physical Chemistry C 113(23):10131-10145, 2009.

(56) References Cited

OTHER PUBLICATIONS

Takanabe, et al. Rate and Selectivity Enhancements Mediated by OH Radicals in the Oxidative coupling of Methane Catalyzed by Mn/NA2 WO4/SiO2 . Angewandte Chemie International Edition 47:7689-7693, 2008.

Tong, et al. Development strategy research of downstream products of ethene in Tianjin. Tianjin Economy, pp. 37-40,1996.

Trautmann, et al. Cryogenic technology for nitrogen rejection from variable content natural gas. Presented at the XIV Convencion Internacional de Gas, Caracas, Venezuela, May 10-12, 2000, 13 pages.

Wang, et al. Autothermal oxidative coupling of methane on the SrCO3/Sm2 O3 catalysts. Catalysis communications 10: 807-810, 2009.

Wang, et al. Comparative study on oxidation of methane to ethane and ethylene over NA2 WO4-Mn/SiO2 catalysts prepared by different methods. Journal of Molecular Catalysis A: Chemical 245:272-277, 2006.

\* cited by examiner

METHODS AND SYSTEMS FOR PERFORMING OXIDATIVE COUPLING OF METHANE

CROSS-REFERENCE TO RELATED APPLICATIONS

This application claims priority to and the benefit of U.S. Provisional Application No. 63/238,816, filed Aug. 31, 2021, the entire content of which is incorporated by reference herein.

FIELD

The present disclosure relates to methods and systems for performing an oxidative coupling of methane reaction to produce $C_{2+}$ compounds. More particularly, the present disclosure relates to methods and systems for performing an oxidative coupling of methane reaction to produce $C_{2+}$ compounds using a low temperature gas mixture feed.

BACKGROUND

It is known that methane and oxygen can be used to produce $C_{2+}$ compounds (e.g., ethylene, ethane) via the oxidative coupling of methane (OCM) reaction. Although extensive research and development has been devoted to OCM technology over the last several decades, a viable OCM process has not yet been commercialized.

One of the primary obstacles to overcome in achieving a commercially viable OCM process has been the high ignition and reaction temperatures required to make the OCM reaction proceed. Conventional methods of performing an OCM reaction typically utilize a high temperature furnace to preheat the reactant feed(s) to the temperature required to ignite or "light-off" the OCM catalyst to initiate the OCM reaction. Operation of the high temperature furnace can be quite expensive and also creates a source of emissions as the high temperature furnace burns fuel (e.g., natural gas) to generate the required heat.

Moreover, mixing the reactant feeds (i.e., methane containing feed and oxygen containing feed) at the high temperatures required to light-off the OCM catalyst and carry out the OCM reaction can create potential process safety and operation issues. For example, mixing the reactant feeds at high temperatures can cause ignition of the mixed reactant gas feed prior to reaching the OCM catalyst bed. Such premature ignition can cause damage to the reactor as well as the OCM catalyst bed. Damage to the catalyst can impede the ability of the catalyst to light-off and initiate the OCM reaction. Furthermore, premature ignition of the mixed reactant gas feed can reduce the selectivity of the OCM reaction due to the conversion of methane to carbon dioxide and carbon monoxide instead of the desired $C_{2+}$ products. In addition, a wide variety of process upsets (e.g., flow upsets, temperature deviations) can lead to premature ignition of the mixed reactant gas feed. Accordingly, mixing the reactant feeds at the high temperatures required to light-off the OCM catalyst and carry out the OCM reaction may result in process safety issues.

SUMMARY

Disclosed herein are methods and systems for performing an oxidative coupling of methane reaction to produce $C_{2+}$ compounds using a low temperature gas mixture feed. By providing the gas mixture feed at a low temperature (i.e., 300° C. or less), process safety is improved by avoiding the aforementioned issues associated with mixing the methane and oxygen reactant feeds at elevated temperatures (e.g., 450° C. or more). In addition, performing an oxidative coupling of methane reaction using a low temperature gas mixture feed obviates the need for a high temperature feed heater furnace and eliminates the furnace-associated air emissions from the process. Furthermore, the methods and systems of the present disclosure can promote the $C_{2+}$ selectivity of the OCM reaction if hydrogen, carbon monoxide, or both are initially combusted preferentially to methane.

In accordance with the invention of the present disclosure, a method of performing an oxidative coupling of methane (OCM) reaction to produce $C_{2+}$ compounds is provided. The method includes introducing a gas mixture feed comprising methane ($CH_4$), oxygen ($O_2$), hydrogen ($H_2$), and carbon monoxide (CO) and having a temperature of less than or equal to 300° C. to an inlet of an OCM reactor. The OCM reactor includes a combustion catalyst and an OCM catalyst. The method also includes contacting the combustion catalyst with the gas mixture feed to combust at least a portion of the gas mixture feed to generate a heated gas mixture having a temperature of at least 450° C. The heated gas mixture contacts the OCM catalyst to initiate an OCM reaction and produce an OCM effluent comprising (i) $C_{2+}$ compounds including ethylene and ethane, and (ii) non-$C_{2+}$ impurities comprising one or more of CO, $CH_4$, $H_2$, and carbon dioxide ($CO_2$).

In accordance with the invention of the present disclosure, a method of performing an oxidative coupling of methane (OCM) reaction to produce $C_{2+}$ compounds is provided. The method includes mixing an oxidant stream comprising oxygen ($O_2$) having a temperature of 0° C. to 250° C. with a hydrocarbon stream comprising methane ($CH_4$), carbon monoxide (CO), and hydrogen ($H_2$) having a temperature of less than or equal to 300° C. to form a gas mixture feed having a temperature of less than or equal to 300° C. Next, the gas mixture feed is introduced to an inlet of an OCM reactor. The OCM reactor includes a combustion catalyst and an OCM catalyst. The method also includes contacting the combustion catalyst with the gas mixture feed to combust at least a portion of the gas mixture feed to generate a heated gas mixture having a temperature of at least 450° C. The heated gas mixture contacts the OCM catalyst to initiate an OCM reaction and produce an OCM effluent comprising (i) $C_{2+}$ compounds including ethylene and ethane, and (ii) non-$C_{2+}$ impurities comprising one or more of CO, $CH_4$, $H_2$, and carbon dioxide ($CO_2$).

In accordance with the invention of the present disclosure, a system for performing an oxidative coupling of methane (OCM) reaction to produce $C_{2+}$ compounds is provided. The system comprises an OCM reactor that includes a combustion catalyst and an OCM catalyst. The OCM reactor receives a gas mixture feed comprising methane ($CH_4$), oxygen ($O_2$), hydrogen ($H_2$), and carbon monoxide (CO) at a temperature of less than or equal to 300° C. The combustion catalyst promotes combustion of at least a portion of the gas mixture feed to generate a heated gas mixture having a temperature of at least 450° C. The OCM catalyst initiates an OCM reaction when contacted by the heated gas mixture to produce an OCM effluent comprising (i) $C_{2+}$ compounds including ethylene and ethane, and (ii) non-$C_{2+}$ impurities comprising one or more of CO, $CH_4$, $H_2$, and carbon dioxide ($CO_2$).

Other aspects and advantages of the present disclosure will be apparent from the description that follows.

DETAILED DESCRIPTION

Figure 1:
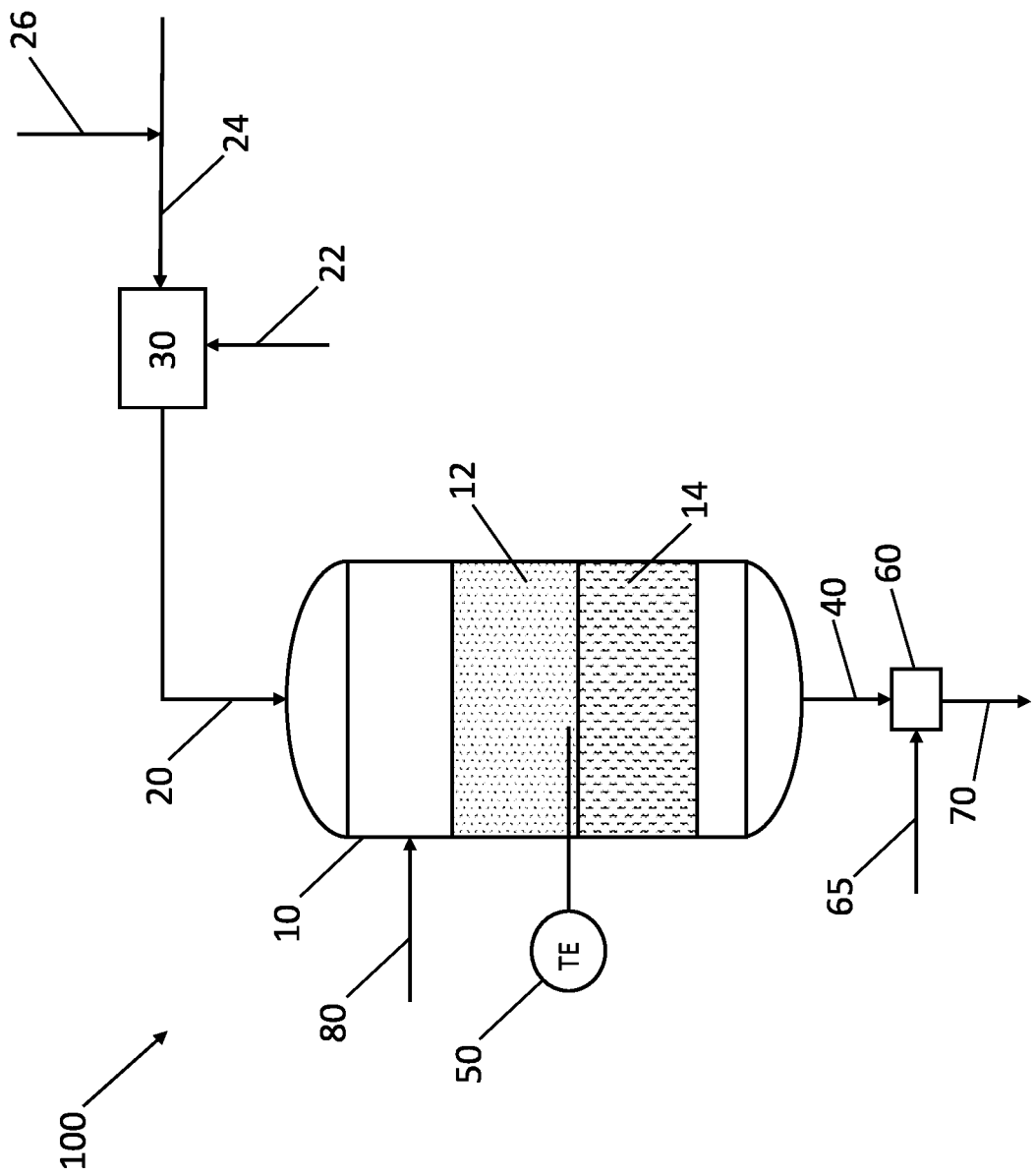
FIG. 1 illustrates a schematic of an exemplary oxidative coupling of methane reactor in accordance with the present disclosure.

Described herein are methods and systems for performing an oxidative coupling of methane reaction to produce $C_{2+}$ compounds using a low temperature gas mixture feed. In accordance with the invention of the present disclosure, an oxidative coupling of methane (OCM) reaction is performed utilizing a gas mixture feed having a temperature of less than or equal to 300° C. The methods and systems of the present disclosure improve the overall safety of the OCM process by avoiding issues associated with mixing methane and oxygen at elevated temperatures (e.g., 450° C. or more). In addition, the methods and systems of the present disclosure obviate the need for a high temperature furnace or preheater typically used in conventional OCM processes, which thereby eliminates the associated furnace/preheater air emissions from the process. Furthermore, the methods and systems of the present disclosure can promote the $C_{2+}$ selectivity of the OCM reaction by preferentially combusting hydrogen, carbon monoxide, or both over methane in the gas mixture feed.

The term "OCM reaction," as used herein, generally refers to an oxidative coupling of methane reaction or process to produce ethylene ($C_2H_4$). An OCM reaction can include the oxidation of methane to a hydrocarbon and water and involves an exothermic reaction. In an OCM reaction, methane can be partially oxidized to one or more $C_{2+}$ compounds, such as ethylene. In an example, an OCM reaction is $2\ CH_4 + O_2 \rightarrow C_2H_4 + 2\ H_2O$. An OCM reaction can yield $C_{2+}$ compounds. An OCM reaction can be facilitated by an OCM catalyst, such as a heterogeneous catalyst. Additional by-products of OCM reactions can include CO, $CO_2$, and $H_2$. Ethane can also react to form ethylene over the OCM catalyst in an OCM reaction.

The terms "$C_{2+}$" and "$C_{2+}$ compound," as used herein, generally refer to a compound comprising two or more carbon atoms, e.g., $C_2$, $C_3$, etc. $C_{2+}$ compounds include, but are not limited to, alkanes, alkenes, and alkynes that contain two or more carbon atoms. Examples of $C_{2+}$ compounds include ethane, ethylene, ethyne, propane, propylene, propyne, and so forth. Similarly, the terms "$C_{3+}$" and "$C_{3+}$ compound," as used herein generally refer to a compound comprising three or more carbon atoms, e.g., $C_3$, $C_4$, $C_5$, etc. $C_{3+}$ compounds include, but are not limited to, alkanes, alkenes, and alkynes that contain two or more carbon atoms. Examples of $C_{3+}$ compounds include propane, propylene, propyne, butane, butene, and so forth.

The term "non-$C_{2+}$ impurities," as used herein, generally refers to material that does not include $C_{2+}$ compounds. Examples of non-$C_{2+}$ impurities, which may be found in certain OCM reaction product streams or effluents include, but are not limited to, nitrogen ($N_2$), oxygen ($O_2$), water ($H_2O$), argon (Ar), hydrogen ($H_2$) carbon monoxide (CO), carbon dioxide ($CO_2$), and methane ($CH_4$).

The term "$C_{2+}$ selectivity," as used herein, generally refers to the percentage of the moles of carbon in methane that are converted into $C_{2+}$ compounds (e.g., ethylene, ethane).

The term "unit," as used herein, generally refers to a unit operation. A unit operation may be one or more basic operations in a process. A unit may have one or more sub-units (or subsystems). Unit operations may involve a physical change or chemical transformation, such as separation, crystallization, evaporation, filtration, polymerization, isomerization, other reactions, or combinations thereof. A unit may include one or more individual components. For example, a separations unit may include one or more separation columns, or an amine unit may include one or more amine columns.

As used herein the term "adiabatic" refers to a system experiencing minimal or ideally no interchange or exchange of thermal energy with the surrounding environment. As used herein "adiabatic" vessels (e.g., reactors) and vessels said to be operating under "adiabatic" conditions refer to vessels having no provision specifically for the removal or addition of thermal energy to or from the system. Notwithstanding the foregoing, it will be appreciated that incidental thermal transfer between the vessel and its environment is contemplated within the context of the foregoing definition. Generally, where an adiabatic vessel is used to contain a reaction that releases thermal energy (i.e., an "exothermic" reaction), a positive temperature profile will be maintained between the reactants added to the vessel and the products removed from the vessel. In other words, the products removed from the vessel will generally be at a temperature above the temperature of the reactants introduced to the vessel since the thermal energy liberated by the reaction can only be substantially removed by the products of the reaction.

The term "substantially $CO_2$-free," as used herein, generally refers to a $CO_2$ molar percentage of less than 1%, including less than 0.5%, less than 0.25%, less than 0.1%, less than 0.05%, and also including 0%.

The term "substantially dry," as used herein, generally refers to a $H_2O$ molar percentage of less than 1%, including less than 0.5%, less than 0.25%, less than 0.1%, less than 0.05%, and also including 0%.

In accordance with the present invention, it has been discovered that an OCM reaction can be performed utilizing a gas mixture feed having a temperature of 300° C. or less by using a combustion catalyst to autothermally heat the gas mixture feed to a temperature sufficient to initiate an OCM reaction when the heated gas mixture contacts an OCM catalyst. The methods and systems of the present disclosure have several advantages over known OCM methods and systems including improved process safety by using a gas mixture feed containing methane and oxygen at a low temperature (i.e., 300° C. or less), less capital equipment and emissions (i.e., no high temperature furnace/preheater or associated emissions), and good $C_{2+}$ selectivity of the OCM reaction.

Reference will now be made to the figures to further describe the methods and systems of the present disclosure. It will be appreciated that the figures and features therein are not necessarily drawn to scale. In the figures, the direction of fluid flow is indicated by arrows. Fluid may be directed from one unit to another with the aid of valves and a fluid flow system. As those of skill in the art will appreciate, such fluid flow systems may include compressors and/or pumps, as well as a control system for regulating fluid flow.

Referring now to FIG. 1, a system 100 for performing an OCM reaction to produce $C_{2+}$ compounds, including ethylene ($C_2H_4$), in accordance with the present disclosure is shown. The system 100 includes an OCM reactor 10 comprising a combustion catalyst 12 and an OCM catalyst 14. In certain aspects, the system 100 can include one or more OCM reactors 10 in series and/or parallel. In certain aspects, the OCM reactor 10 is an adiabatic reactor. In certain aspects, the OCM reactor 10 operates under adiabatic conditions. In certain aspects, the OCM reactor 10 is an isothermal reactor. In certain aspects, the OCM reactor 10 operates under isothermal conditions. The OCM reactor 10 may operate at a pressure of 0 kPa (gauge) to 2,000 kPa (gauge), including a pressure of 100 kPa (gauge) to 2,000 kPa (gauge), a pressure of 250 kPa (gauge) to 2,000 kPa (gauge), a pressure of 500 kPa (gauge) to 2,000 kPa (gauge), a pressure of 700 kPa (gauge) to 1,500 kPa (gauge), and also including a pressure of 750 kPa (gauge) to 1,250 kPa (gauge).

As seen in FIG. 1, the OCM reactor 10 receives a gas mixture feed 20 at an inlet of the OCM reactor 10. The gas mixture feed 20 comprises methane ($CH_4$), oxygen ($O_2$), hydrogen ($H_2$), and carbon monoxide (CO). The gas mixture feed 20 may be formed by mixing together a hydrocarbon stream 22 comprising $CH_4$, $H_2$, and CO and an oxidant stream 24 comprising $O_2$. In certain aspects of the methods and systems of the present disclosure, the oxidant stream 24 is provided by an air stream or an $O_2$ stream that is generated by an air separation unit. In certain aspects of the methods and systems of the present disclosure, the oxidant stream 24 further comprises steam, which may be injected or otherwise added into the oxidant stream 24 via line 26. In certain aspects, the hydrocarbon stream 22 is mixed with the oxidant stream 24 in a mixing device 30. The mixing device 30 may be any known device suitable for mixing together a first gas stream comprising hydrocarbons and a second gas stream comprising oxygen such as, for example, the mixing device described in U.S. Pat. No. 3,706,534. In certain aspects, the mixing device 30 comprises process piping or a mixing tee.

In accordance with the methods and systems of the present disclosure, the gas mixture feed 20 is introduced in the OCM reactor 10 at a temperature of less than or equal to 300° C. In certain aspects, the gas mixture feed 20 is introduced in the OCM reactor 10 at a pressure of 200 kPa (gauge) to 1,400 kPa (gauge), including a pressure of 500 kPa (gauge) to 1,200 kPa (gauge), 600 kPa (gauge) to 1,100 kPa (gauge), 700 kPa (gauge) to 1,000 kPa (gauge), and also including a pressure of 750 kPa (gauge) to 950 kPa (gauge). In certain aspects, the gas mixture feed 20 has a temperature of 15° C. to 300° C. at the inlet of the OCM reactor 10, including a temperature of 50° C. to 300° C., 100° C. to 300° C., 100° C. to 250° C., 100° C. to 225° C., 100° C. to 200° C., 100° C. to 175° C., 100° C. to 150° C., 100° C. to 125° C., 125° C. to 300° C., 150° C. to 300° C., 175° C. to 300° C., 200° C. to 300° C., 225° C. to 300° C., 250° C. to 300° C. and also including a temperature of 275° C. to 300° C. at the inlet of the OCM reactor 10. In certain aspects, the hydrocarbon stream 22 used to form the gas mixture feed 20 has a temperature of less than or equal to 300° C., including a temperature of 15° C. to 300° C., 25° C. to 300° C., 50° C. to 300° C., 75° C. to 300° C., 100° C. to 300° C., 125° C. to 250° C., 150° C. to 225° C., 175° C. to 200° C., 15° C. to 250° C., 15° C. to 200° C., 15° C. to 150° C., 15° C. to 100° C., 15° C. to 75° C., and also including a temperature of 15° C. to 50° C. In certain aspects, the oxidant stream 24 used to form the gas mixture feed 20 has a temperature of 0° C. to 250° C., including a temperature of 10° C. to 250° C., 20° C. to 250° C., 30° C. to 200° C., 30° C. to 150° C., 30° C. to 100° C., 30° C. to 50° C., 40° C. to 250° C., 100° C. to 250° C., 150° C. to 250° C., 200° C. to 250° C., 0° C. to 50° C., and also including a temperature of 0° C. to 30° C.

By providing the gas mixture feed 20 to the OCM reactor 10 at a relatively low temperature, the methods and systems of the present disclosure improve the safety of the OCM process by essentially eliminating the chances of the gas mixture feed 20 prematurely igniting. While beneficial, the low temperature of the gas mixture feed 20 creates an obstacle to successfully performing an OCM reaction, namely, achieving the minimum temperature required to light-off or activate an OCM catalyst 14 to initiate an OCM reaction. Depending on the OCM catalyst 14, a minimum temperature of at least 450° C. (e.g., 450° C. to 700° C.) and more typically 500° C. to 700° C. is required to achieve light-off and initiate an OCM reaction.

Accordingly, to overcome this obstacle, the methods and systems of the present disclosure utilize a combustion catalyst 12 to autothermally heat the gas mixture feed 20 within the OCM reactor 10. When contacted by the gas mixture feed 20, the combustion catalyst 12 promotes combustion of at least a portion of the gas mixture feed 20 to generate a heated gas mixture having a temperature of at least 450° C. In certain aspects of the methods and systems of the present disclosure, when contacted by the gas mixture feed 20, the combustion catalyst 12 promotes combustion of at least a portion of the gas mixture feed 20 to generate a heated gas mixture having a temperature of 450° C. to 700° C., including a temperature of 500° C. to 700° C., 500° C. to 650° C., a temperature of 500° C. to 600° C., and also including a temperature of 525° C. to 600° C. Accordingly, the combustion catalyst 12 can be used to create a temperature difference between the temperature of the gas mixture feed 20 at the inlet of the OCM reactor 10 and the temperature of the heated gas mixture of 150° C. to 600° C., including a temperature difference of 200° C. to 550° C., 250° C. to 550° C., 300° C. to 500° C., and also including a temperature difference of 350° C. to 500° C.

The combustion catalyst 12 can be any catalyst composition now known or known in the future that is capable of combusting at least a portion of one or more components of the gas mixture feed 20 (e.g., $H_2$, CO, $CH_4$). In certain aspects of the methods and systems of the present disclosure, the combustion catalyst 12 comprises at least one of a metal, a metal oxide, or a mixed metal oxide. Exemplary metals, metal oxides, and mixed metal oxides suitable for use as the combustion catalyst 12 of the present disclosure include, but are not limited to, platinum, platinum oxide, chromium, chromium(II) oxide, chromium(III) oxide, chromium (VI) oxide, copper, copper(I) oxide, copper(II) oxide, copper(III) oxide, palladium, palladium(II) oxide, cobalt, cobalt(II) oxide, cobalt(III) oxide, iron, iron(II) oxide, iron(III) oxide, manganese, manganese(II) oxide, manganese(III) oxide, gold, gold(III) oxide, cerium, cerium(IV) oxide, tin, tin(II) oxide, tin(IV) oxide, bismuth, bismuth(III) oxide, indium, indium(III) oxide, molybdenum, molybdenum(IV) oxide, molybdenum(VI) oxide, antimony, antimony(III) oxide, lanthanum, lanthanum(III) oxide, aluminum, silver, osmium, tungsten, lead, zinc, nickel, rhodium, ruthenium, thallium, tellurium, germanium, gadolinium, $Bi_2Mo_3O_{12}$, $In_2Mo_3O_{12}$, $Al_2Mo_3O_{12}$, $Fe_2Mo_3O_{12}$, $Cr_2Mo_3O_{12}$, $La_2Mo_3O_{12}$, $Ce_2Mo_3O_{12}$, or combinations thereof. In certain aspects, the combustion catalyst 12 used in the methods and systems of the present disclosure may be in the form of loose catalyst, agglomerated catalyst, sintered catalyst, catalyst pressed or otherwise formed into various shapes such as rings, saddles, spoked wheels, snowflakes, and the like that provide a high ratio of exposed surface area to volume. In certain aspects, the combustion catalyst 12 used in the methods and systems of the present disclosure may be affixed, bonded, or otherwise attached to a substrate or support, which may or may not be inert, that provides structural strength and/or form to the catalyst. Exemplary substrates or supports to which the combustion catalyst 12 may be affixed, bonded, or otherwise attached include, but are not limited to, silica, alumina, titania, zirconia, ceria, hafnia, cordierite, silicon carbide, aluminum hydroxide, calcium aluminates (e.g., tricalcium aluminate, monocalcium aluminate), and zeolites (e.g., ZSM-5 zeolite, Y zeolite, MCM-41 zeolite).

In certain aspects of the methods and systems of the present disclosure, the combustion catalyst 12 selectively or preferentially combusts $H_2$, CO, or both over $CH_4$. Such a combustion catalyst 12 is referred to hereinafter as a "selective combustion catalyst." The selective combustion catalyst can comprise any one or combination of the metals, metal oxides, or mixed metal oxides described above that selectively or preferentially combust $H_2$, CO, or both over $CH_4$. In certain aspects of the methods and systems of the present disclosure, the selective combustion catalyst comprises at least one of platinum, palladium, gold, bismuth, tin, platinum-gold, platinum-tin, palladium(II) oxide, ruthenium, bismuth(III) oxide, antimony(III) oxide, indium(III) oxide, molybdenum(VI) oxide, $Bi_2Mo_3O_{12}$, $In_2Mo_3O_{12}$, $Al_2Mo_3O_{12}$, $Fe_2Mo_3O_{12}$, $Cr_2Mo_3O_{12}$, $La_2Mo_3O_{12}$, $Ce_2Mo_3O_{12}$, or combinations thereof. In certain aspects, the selective combustion catalyst may be in the form of loose catalyst, agglomerated catalyst, sintered catalyst, catalyst pressed or otherwise formed into various shapes such as rings, saddles, spoked wheels, snowflakes, and the like that provide a high ratio of exposed surface area to volume. In certain aspects, the selective combustion catalyst may be affixed, bonded, or otherwise attached to a substrate or support, which may or may not be inert, that provides structural strength and/or form to the catalyst. Exemplary substrates or supports to which the selective combustion catalyst may be affixed, bonded, or otherwise attached include, but are not limited to, silica, alumina, titania, zirconia, ceria, hafnia, cordierite, silicon carbide, aluminum hydroxide, calcium aluminates (e.g., tricalcium aluminate, monocalcium aluminate), and zeolites (e.g., ZSM-5 zeolite, Y zeolite, MCM-41 zeolite).

By using a selective combustion catalyst, less $CH_4$ in the gas mixture feed 20 is consumed or combusted when autothermally raising the temperature of the gas mixture feed 20, which results in more $CH_4$ being available to participate in the OCM reaction. As a result, the selectivity of the OCM reaction for converting $CH_4$ to $C_{2+}$ compounds (i.e., $C_{2+}$ selectivity) can be maintained or improved.

In certain aspects of the methods and systems of the present disclosure, the OCM reaction has a $C_{2+}$ selectivity of at least 35%, at least 40%, at least 45%, at least 50%, at least 55%, at least 60%, at least 65%, or at least 70%. In certain aspects of the methods and systems of the present disclosure, the OCM reaction has a $C_{2+}$ selectivity of 35% to 85%, including a $C_{2+}$ selectivity of 40% to 85%, 50% to 85%, 60% to 85%, and also including a $C_{2+}$ selectivity of 70% to 85%.

In addition to the combustion catalyst 12, the OCM reactor 10 also includes an OCM catalyst 14 to facilitate an OCM reaction to produce an OCM effluent 40 comprising $C_{2+}$ compounds including $C_2H_4$ and $C_2H_6$ and non-$C_{2+}$ impurities comprising one or more of CO, $CH_4$, $H_2$, and carbon dioxide ($CO_2$). The OCM catalyst 14 may be any catalyst composition now known or known in the future that facilitates an OCM reaction, such as the catalysts described in, for example, U.S. Pat. Nos. 8,921,256, 8,962,517, and 9,718,054, the full disclosures of which are incorporated herein by reference in their entirety. In certain aspects, the OCM catalyst 14 used in the methods and systems of the present disclosure may be in the form of loose catalyst, agglomerated catalyst, sintered catalyst, catalyst pressed or otherwise formed into various shapes such as rings, saddles, spoked wheels, snowflakes, and the like that provide a high ratio of exposed surface area to volume. In certain aspects, the OCM catalyst 14 used in the methods and systems of the present disclosure may be affixed, bonded, or otherwise attached to a substrate or support, which may or may not be inert, that provides structural strength and/or form to the catalyst.

When contacted by the heated gas mixture, the OCM catalyst 14 becomes activated (i.e., achieves light-off) and initiates an OCM reaction to produce the OCM effluent 40 comprising $C_{2+}$ compounds including $C_2H_4$ and $C_2H_6$ and non-$C_{2+}$ impurities comprising one or more of CO, $CH_4$, $H_2$, and $CO_2$. Because the OCM reaction is exothermic, the temperature at which the OCM reaction is performed and/or maintained is typically higher than the temperature of the heated gas mixture used to activate or light-off the OCM catalyst 14. In certain aspects, the OCM reaction is performed and/or maintained at a temperature of 450° C. to 950° C., including a temperature of 500° C. to 950° C., 550° C. to 950° C., 600° C. to 950° C., 650° C. to 950° C., 700° C. to 950° C., 750° C. to 950° C., 800° C. to 950° C., 850° C. to 950° C., and also including a temperature of 875° C. to 925° C. The OCM effluent 40 exiting the OCM reactor 10 will generally have a temperature corresponding to that of the OCM reaction temperature (i.e., 450° C. to 950° C.) and can be directed to downstream units and/or a separations subsystem for additional processing as described herein.

The combustion catalyst 12 and the OCM catalyst 14 can be arranged within the OCM reactor 10 in a variety of ways. For example, in certain aspects, the OCM reactor 10 can include a first catalyst bed containing the combustion catalyst 12 and a second catalyst bed containing the OCM catalyst 14 downstream of the first catalyst bed, as illustrated in FIG. 1. In certain aspects, the OCM reactor 10 can include a single catalyst bed comprising at least one layer of the combustion catalyst 12 and at least one layer of the OCM catalyst 14. In certain aspects, the OCM reactor 10 can include a single catalyst bed that comprises a mixture of the combustion catalyst 12 and the OCM catalyst 14. The OCM reactor 10 can also include one or more layers or beds of inert material (not shown), which may function as a physical support for the catalysts 12, 14 in a catalyst bed. In certain aspects, the OCM reactor 10 can include a first catalyst bed containing the combustion catalyst 12 and an inert material, either as one or more distinct layers or as a mixture, and a second catalyst bed containing the OCM catalyst 14.

With continued reference to FIG. 1, the OCM reactor 10 may comprise one or more temperature elements 50 to provide an indication of temperature within the OCM reactor 10. The temperature element 50 may be any suitable temperature measuring device including, but not limited to, a thermocouple and a resistance temperature detector (RTD). As seen in FIG. 1, a temperature element 50 is located in the combustion catalyst 12 upstream of the OCM catalyst 14. For example, where the OCM reactor 10 includes a first catalyst bed comprising a combustion catalyst 12 and a second catalyst bed comprising an OCM catalyst 14, the temperature element 50 is located proximate an end of the first catalyst bed and upstream of the second catalyst bed. In another example, where the OCM reactor 10 includes a single catalyst bed comprising a layer of combustion catalyst 12 upstream of a layer of OCM catalyst, the temperature element 50 is located in the layer of combustion catalyst 12 proximate an interface between the layer of combustion catalyst 12 and the layer of OCM catalyst 14. The temperature element 50 can be used to provide one or more signals indicative of a temperature of the heated gas mixture prior to the heated gas mixture contacting the OCM catalyst 14. The temperature element 50 can be part of a control system operative to maintain the temperature of the heated gas mixture at a desired setpoint (e.g., the minimum OCM catalyst light-off temperature) by, for example, controlling or otherwise adjusting a temperature of the hydrocarbon stream 22, the oxidant stream 24, or both.

In certain aspects, the methods and systems of the present disclosure include a post-bed cracking (PBC) unit 60 for generating olefins (e.g., $C_2H_4$) from alkanes (e.g., $C_2H_6$, $C_3H_8$). The PBC unit 60 can be disposed downstream of the OCM reactor 10, as illustrated in FIG. 1. The PBC unit 60 may be a separate reactor, or the PBC unit 60 may be included as a section of the OCM reactor 10 (e.g., a section downstream of the OCM catalyst 14 in the same vessel). As the OCM reaction is exothermic and generates heat, the heat generated by the OCM reaction can be used to crack alkanes (e.g., $C_2H_6$) to olefins (e.g., $C_2H_4$). The PBC unit 60 may perform the cracking at a temperature of 600° C. to 1,000° C., including a temperature of 700° C. to 1,000° C., 750° C. to 1,000° C., 775° C. to 1,000° C., and also including a temperature of 800° C. to 950° C.

The PBC unit 60 can be used to crack additional external alkanes 65 (e.g., $C_2H_6$, $C_3H_8$) beyond those contained in the OCM effluent 40. The heat capacity in the OCM effluent 40 can be sufficient to crack some amount of additional external alkanes 65. The additional external alkanes 65 can be provided from a recycle stream of the process or an entirely separate source of alkanes. The external alkanes 65 can be heated prior to injection into the PBC unit 60. The external alkanes 65 can be heated by, for example, heat exchange with the OCM reactor 10 and/or the OCM effluent 40, or another process stream. A PBC effluent 70 exits the PBC unit 60 and includes a greater concentration of olefins (e.g., $C_2H_4$) and $H_2$ as compared to the OCM effluent 40.

In certain aspects, the methods and systems of the present disclosure include injecting an ignition component 80 into the OCM reactor 10. The ignition component 80 can be any substance that has a lower autoignition temperature than $CH_4$ such as, for example, dimethyl ether or methanol. The ignition component 80 can be provided to the OCM reactor 10 as an additional means (i.e., via combustion of the ignition component 80) to increase the temperature of the gas mixture feed 20. Although FIG. 1 illustrates the ignition component 80 being injected directly into the OCM reactor 10, the ignition component 80 could also be added to one or more of the gas mixture feed 20, the hydrocarbon stream 22, or the oxidant stream 24.

Figure 2:
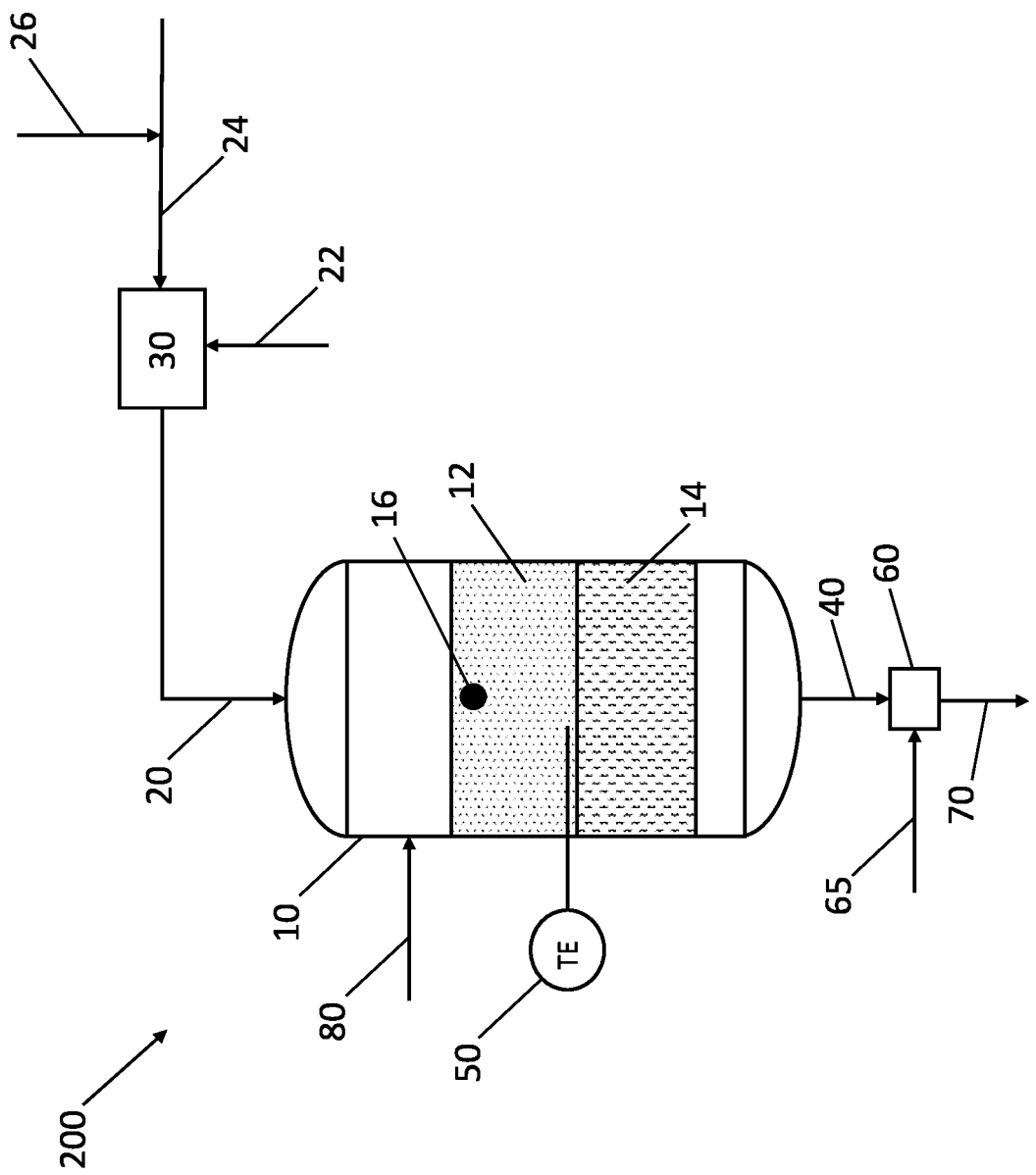
FIG. 2 illustrates a schematic of an exemplary oxidative coupling of methane reactor in accordance with the present disclosure.

Referring now to FIG. 2, a system 200 for performing an OCM reaction to produce $C_{2+}$ compounds, including ethylene ($C_2H_4$), in accordance with the present disclosure is shown. The system 200 illustrated in FIG. 2 is similar to the system 100 depicted in FIG. 1 and like numerals are used in FIG. 2 to identify like components. The primary difference between the system 200 illustrated in FIG. 2 and the system 100 illustrated in FIG. 1 is that the OCM reactor 10 of system 200 comprises at least one ignition source 16.

The at least one ignition source 16 promotes ignition of components (e.g., $H_2$, CO, or both) of the gas mixture feed 20. As seen in FIG. 2, the at least one ignition source 16 is in contact with the combustion catalyst 12 and can provide a localized ignition to assist operation of the combustion catalyst 12 in generating the heated gas mixture. In certain aspects, the at least one ignition source 16 comprises at least one of a steam heated pipe, an electrically powered cartridge heater or other electronic igniter. The ignition source 16 can operate to provide a sufficient temperature (e.g., 400° C. to 600° C.) to cause ignition of one or more components of the gas mixture feed 20 in a localized area of the combustion catalyst 12 as a mechanism for assisting the combustion catalyst 12 in promoting combustion of at least a portion of gas mixture feed 20 to generate the heated gas mixture. In certain aspects, the at least one ignition source 16 (e.g., steam heated pipe, electrically powered cartridge heater or other electronic igniter) can be positioned proximate to and upstream of the combustion catalyst 12 (i.e., not in direct contact with the combustion catalyst 12) to provide a localized ignition to assist operation of the combustion catalyst 12 in generating the heated gas mixture.

In the system 200 illustrated in FIG. 2, the OCM reactor 10 may include a temperature element 50 located in the combustion catalyst 12 upstream of the OCM catalyst 14 as described above with respect to the system 100 shown in FIG. 1. In the system 200, the temperature element 50 can be part of a control system operative to maintain the temperature of the heated gas mixture at a desired setpoint (e.g., the minimum OCM catalyst light-off temperature) by, for example, controlling or otherwise adjusting a temperature locally imparted by the at least one ignition source 16 (e.g., by adjusting an amount of power provided to the one or more electrically powered cartridge heaters, by adjusting a temperature of the one or more steam heated pipes). In certain aspects, in addition to controlling or otherwise adjusting the temperature imparted by the at least one ignition source 16, a temperature of the hydrocarbon stream 22, the oxidant stream 24, or both may be controlled or otherwise adjusted to maintain the temperature of the heated gas mixture at the desired setpoint.

Figure 3:
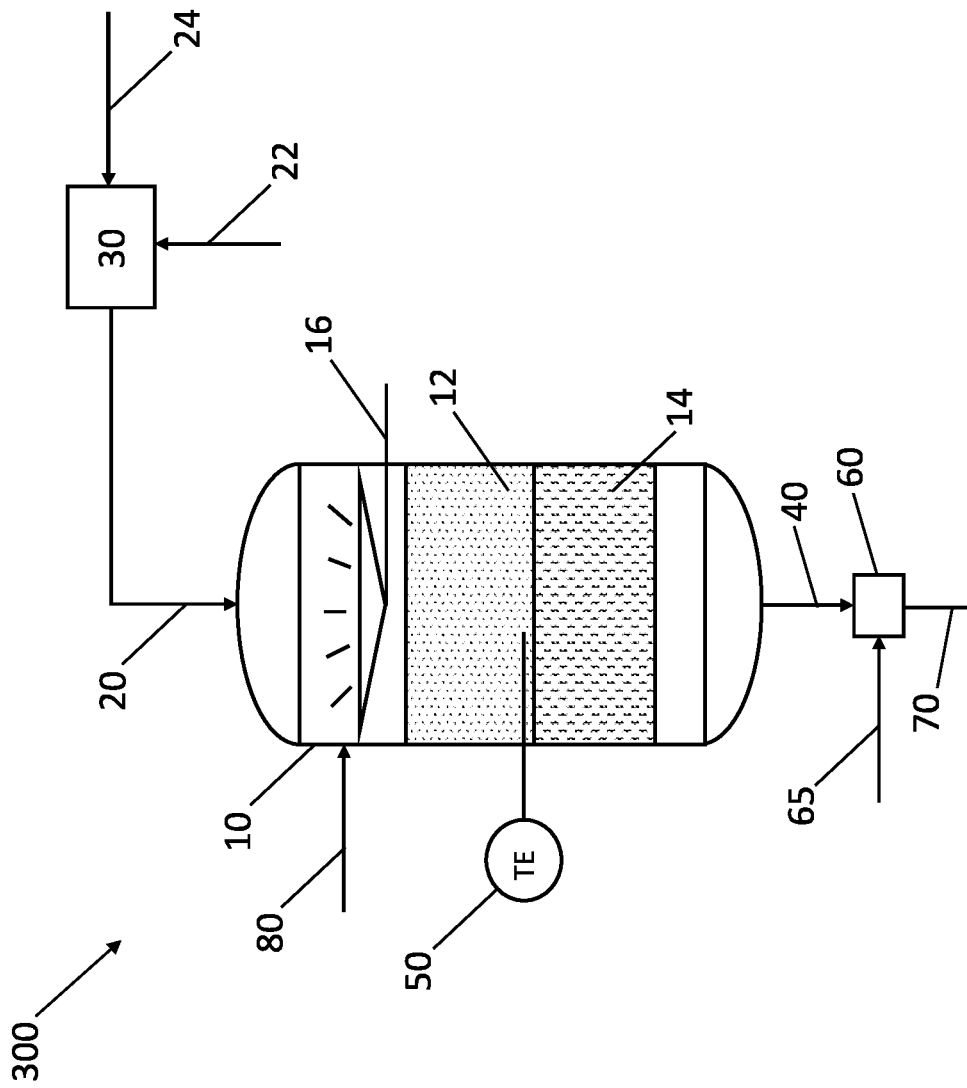
FIG. 3 illustrates a schematic of an exemplary oxidative coupling of methane reactor in accordance with the present disclosure.

Referring now to FIG. 3, a system 300 for performing an OCM reaction to produce $C_{2+}$ compounds, including ethylene ($C_2H_4$), in accordance with the present disclosure is shown. The system 300 illustrated in FIG. 3 is similar to the systems 100, 200 depicted in FIGS. 1 and 2 and like numerals are used in FIG. 3 to identify like components. The primary difference between the system 300 illustrated in FIG. 3 and the system 200 illustrated in FIG. 2 resides in the type and configuration of the least one ignition source 16.

As seen in FIG. 3, the at least one ignition source 16 is positioned upstream of both the combustion catalyst 12 and the OCM catalyst 14. In the system 300 illustrated in FIG. 3, the at least one ignition source 16 comprises a superheated steam injector that injects superheated steam at a temperature of 600° C. to 1,000° C. into the OCM reactor 10. In certain aspects, the superheated steam has a pressure of 400 kPa (gauge) to 3,000 kPa (gauge). In certain aspects of the methods and systems of the present disclosure, superheated steam is injected into the OCM reactor 10 at a temperature of 625° C. to 1,000° C., including a temperature of 650° C. to 950° C., a temperature of 675° C. to 900° C., 700° C. to 900° C., and also including a temperature of 750° C. to 850° C. The injection of superheated steam can cause ignition of one or more components of the gas mixture feed 20 to assist operation of the combustion catalyst 12 in generating the heated gas mixture. In addition, because the system 300 includes the injection of superheated steam into the OCM reactor 10, the optional steam 26 added to the oxidant stream 24 illustrated in FIGS. 1 and 2 is unnecessary.

In the system 300 illustrated in FIG. 3, the OCM reactor 10 may include a temperature element 50 located in the combustion catalyst 12 upstream of the OCM catalyst 14 as described above with respect to system 100, 200 shown in FIGS. 1 and 2. In the system 300, the temperature element 50 can be part of a control system operative to maintain the temperature of the heated gas mixture at a desired setpoint (e.g., the minimum OCM catalyst light-off temperature) by, for example, controlling or otherwise adjusting a temperature the superheated steam injected into the OCM reactor 10. In certain aspects, in addition to controlling or otherwise adjusting the temperature of the superheated stem injected into the OCM reactor 10, a temperature of the hydrocarbon stream 22, the oxidant stream 24, or both may be controlled or otherwise adjusted to maintain the temperature of the heated gas mixture at the desired setpoint.

Figure 4:
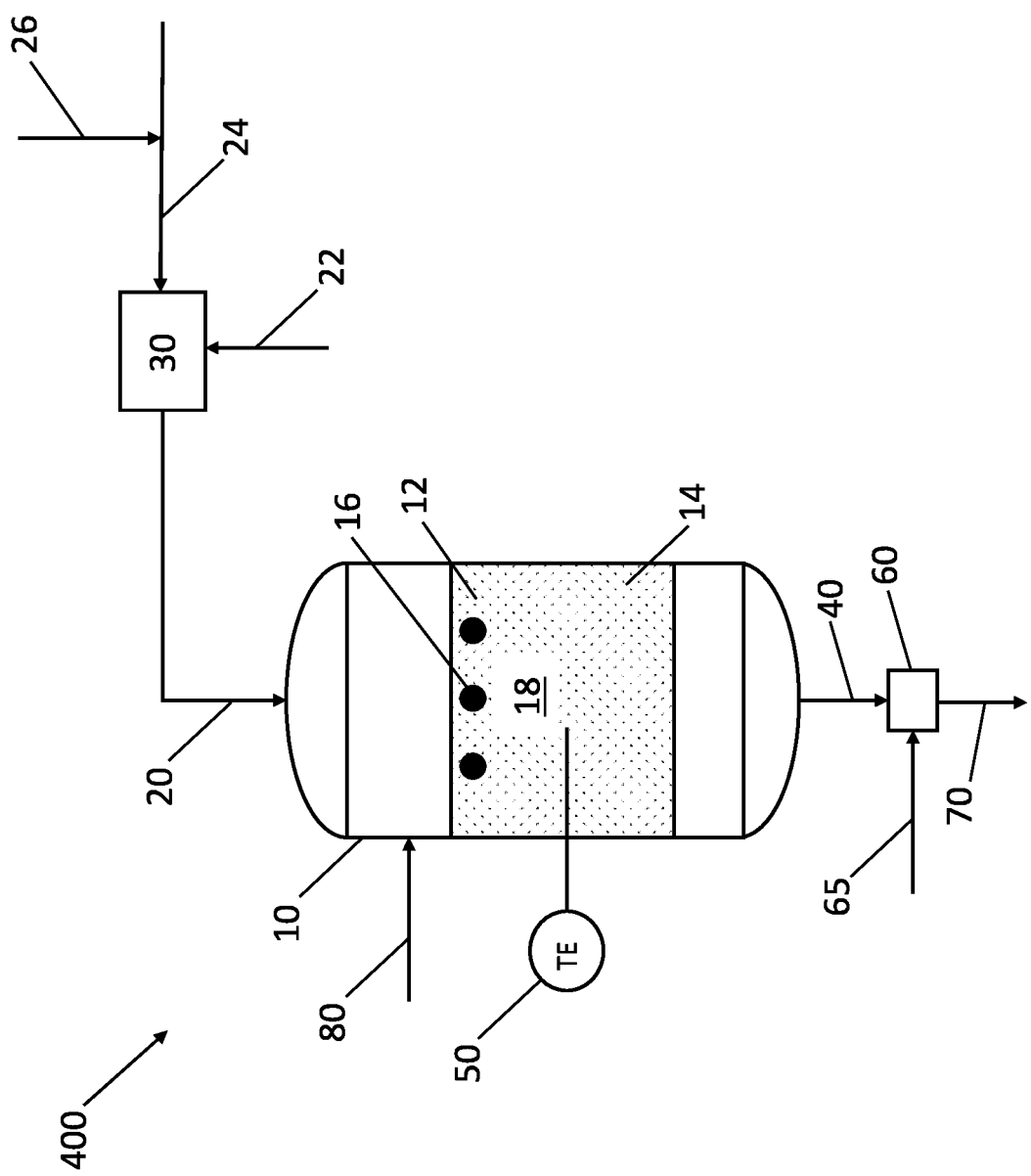
FIG. 4 illustrates a schematic of an exemplary oxidative coupling of methane reactor in accordance with the present disclosure.

Referring now to FIG. 4, a system 400 for performing an OCM reaction to produce $C_{2+}$ compounds, including ethylene ($C_2H_4$), in accordance with the present disclosure is shown. The system 400 illustrated in FIG. 4 is similar to the systems 100, 200, 300 depicted in FIGS. 1-3 and like numerals are used in FIG. 4 to identify like components.

As seen in FIG. 4, the OCM reactor 10 includes a single catalyst bed 18 that comprises a combustion catalyst 12 and an OCM catalyst 14 as well as at least one ignition source 16 located in the catalyst bed 18. The catalyst bed 18 can be configured such that the at least one ignition source 16 (e.g., steam heated pipe, electrically powered cartridge heater or other electronic igniter) is encompassed by the combustion catalyst 12. Alternatively, the at least one ignition source 16 (e.g., steam heated pipe, electrically powered cartridge heater or other electronic igniter) can be positioned proximate to and upstream of the catalyst bed 18 (i.e., not in direct contact with the catalyst bed 18). In certain aspects, the catalyst bed 18 can comprise at least one layer of the combustion catalyst 12 and at least one layer of the OCM catalyst 14. In certain aspects, the catalyst bed 18 can comprise a mixture of the combustion catalyst 12 and the OCM catalyst 14.

In the system 400 illustrated in FIG. 4, the OCM reactor 10 may include a temperature element 50 located in the catalyst bed 18. The temperature element 50 can be part of a control system operative to maintain a desired temperature profile across and/or throughout the catalyst bed 18 by, for example, controlling or otherwise adjusting a temperature locally imparted by the at least one ignition source 16 (e.g., by adjusting an amount of power provided to one or more electrically powered cartridge heaters, by adjusting a temperature of one or more steam heated pipes). In certain aspects, in addition to controlling or otherwise adjusting the temperature locally imparted by the at least one ignition source 16, a temperature of the hydrocarbon stream 22, the oxidant stream 24, or both may be controlled or otherwise adjusted to maintain the desired temperature profile across and/or throughout the catalyst bed 18.

Figure 5:
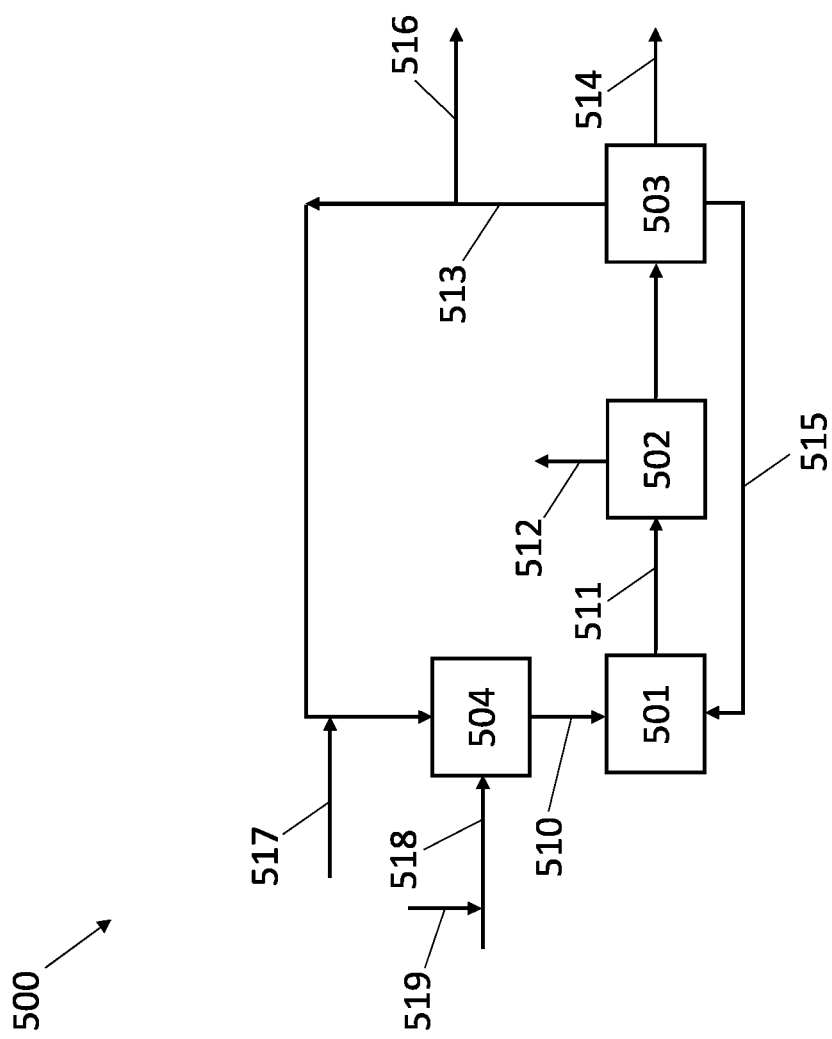
FIG. 5 illustrates a block flow diagram of an exemplary system for performing an oxidative coupling of methane reaction to produce $C_{2+}$ compounds in accordance with the present disclosure.

Referring now to FIG. 5, a block flow diagram of a system 500 for performing an OCM reaction to produce $C_{2+}$ compounds, including ethylene ($C_2H_4$), in accordance with the present disclosure is shown. The system 500 comprises an OCM subsystem 501, an optional $CO_2$ removal unit 502, and a separations subsystem 503. The OCM subsystem 501 is fluidly coupled to the separations subsystem 503 and is configured to receive a gas mixture feed 510 having a temperature of less than or equal to 300° C. and comprising methane ($CH_4$), oxygen ($O_2$), hydrogen ($H_2$), and carbon monoxide (CO) and to generate an OCM effluent 511 comprising $C_{2+}$ compounds including $C_2H_4$ and $C_2H_6$ and non-$C_{2+}$ impurities comprising one or more of CO, $CO_2$, $H_2$, and $CH_4$. The separations subsystem 503 is downstream of and fluidly coupled to the OCM subsystem 501 and is configured to receive the OCM effluent 511 and to separate the OCM effluent 511 into at least a first stream 513 comprising CO, $H_2$, and $CH_4$ and a second stream (not shown) comprising $C_{2+}$ compounds including $C_2H_4$ and $C_2H_6$. The second stream may be further separated in the separations subsystem 503 to produce a third stream 514 comprising $C_2H_4$ and a fourth stream 515 comprising $C_2H_6$.

In accordance with the methods and systems of the present disclosure, the OCM subsystem 501 includes an OCM reactor comprising a combustion catalyst and an OCM catalyst. In certain aspects, the OCM subsystem 501 includes an OCM reactor comprising a combustion catalyst and an OCM catalyst and a PBC unit. The OCM reactor and PBC unit of the OCM subsystem 501 may be configured the same as any one or more of the OCM reactors 10 and PBC units 60 previously described herein with reference to FIGS. 1-4.

As seen in FIG. 5, the gas mixture feed 510 is directed to the OCM subsystem 501 to generate an OCM effluent 511 comprising $C_{2+}$ compounds including $C_2H_4$ and $C_2H_6$ and non-$C_{2+}$ impurities comprising one or more of CO, $CO_2$, $H_2$, and $CH_4$. The OCM effluent 511 can be directed to a separations subsystem 503 to separate the OCM effluent 511 into at least a first stream 513 comprising CO, $H_2$, and $CH_4$ and a second stream comprising $C_{2+}$ compounds including $C_2H_4$ and $C_2H_6$. As seen in FIG. 5, the first stream 513 comprising CO, $H_2$, and $CH_4$, or a portion thereof, can be recycled to the OCM subsystem 501 to facilitate generation of the gas mixture feed 510. In accordance with certain aspects of the methods and systems of the present disclosure, at least a portion of the first stream 513 may be purged via stream 516 to prevent the accumulation of inert components (e.g., $N_2$) in the system 500. In addition, the separations subsystem 503 can separate the second stream comprising $C_{2+}$ compounds into a third stream 514 comprising $C_2H_4$ product and a fourth stream 515 comprising $C_2H_6$. As shown in FIG. 5, the fourth stream 515 comprising $C_2H_6$ can be directed to the OCM subsystem 501 (e.g., to the OCM reactor and/or to the PBC unit) to produce additional $C_2H_4$ and $H_2$ by cracking the $C_2H_6$.

The separations subsystem 503 may comprise any number of separation units or utilize any combination of separation technologies suitable for separating the products of an OCM reaction. For example, the separations subsystem 503 may separate the OCM effluent 511 with the aid of cryogenic separation, pressure swing adsorption, temperature swing adsorption, membrane separation, adsorbents, and combinations thereof. Examples of separations subsystems 503 suitable for implementation in the methods and systems of the present disclosure are described in, for example, WO 2014/011646 A1, WO 2013/106771 A2, WO 2015/106023 A1, WO 2017/065947 A1, and WO 2018/118105 A1, the full disclosures of which are incorporated herein by reference in their entirety.

As seen in FIG. 5, in accordance with some aspects of the methods and systems of the present disclosure, the system 500 comprises a $CO_2$ removal unit 502 fluidly coupled to the OCM subsystem 501 and the separations subsystem 503. The $CO_2$ removal unit 502 is configured to remove $CO_2$ from the OCM effluent 511 via stream 512 and to direct the substantially $CO_2$-free OCM effluent to the separations subsystem 503. The $CO_2$ removal unit 502 may comprise any known technology suitable for removing $CO_2$ from a process stream. Examples of suitable $CO_2$ removal technologies include, but are not limited to, an amine absorber system, pressure swing adsorption, temperature swing adsorption, membrane separation, solvent separation, and cryogenic separation.

While FIG. 5 illustrates a $CO_2$ removal unit 502 positioned downstream of the OCM subsystem 501 and upstream of the separations subsystem 503, it is contemplated that $CO_2$ contained in the OCM effluent 501 may be removed via the separations subsystem 503, thereby eliminating the need for a $CO_2$ removal unit 502. Such an arrangement would be particularly suitable in systems where the separations subsystem 503 is based on adsorption technology.

In accordance with certain aspects of the methods and systems of the present disclosure, the system 500 comprises a mixing device 504 fluidly coupled to the OCM subsystem 501 and to the separations subsystem 503, as shown in FIG. 5. The mixing device 504 facilitates formation of the gas mixture feed 510 that is directed to the OCM subsystem 501. As seen in FIG. 5, the mixing device 504 receives a hydrocarbon stream that comprises at least a portion of the first stream 513 from the separations subsystem 503 and an oxidant stream 518 comprising oxygen. In certain aspects of the methods and systems of the present disclosure, a methane or natural gas stream 517 can be added to the first stream 513 to form the hydrocarbon stream that is directed to the mixing device 504. In certain aspects of the methods and systems of the present disclosure, the oxidant stream 518 is provided by an air stream or an $O_2$ stream that is generated by, for example, an air separation unit, a membrane, or a water electrolysis unit. In certain aspects of the methods and systems of the present disclosure, the oxidant stream 518 further comprises steam, which may be injected or otherwise added into the oxidant stream 518 via line 519. The mixing device 504 may be any known device suitable for mixing together a first gas stream comprising hydrocarbons and a second gas stream comprising oxygen such as, for example, the mixing device described in U.S. Pat. No. 3,706,534. In certain aspects, the mixing device 504 comprises process piping or a mixing tee.

The gas mixture feed 510 has a temperature of less than or equal to 300° C. when exiting the mixing device 504 and entering an inlet of an OCM reactor of the OCM subsystem 501. In certain aspects, the gas mixture feed 510 has a temperature of 15° C. to 300° C. at an inlet of the OCM reactor 10, including a temperature of 50° C. to 300° C., 100° C. to 300° C., 100° C. to 250° C., 100° C. to 225° C., 100° C. to 200° C., 100° C. to 175° C., 100° C. to 150° C., 100° C. to 125° C., 125° C. to 300° C., 150° C. to 300° C., 175° C. to 300° C., 200° C. to 300° C., 225° C. to 300° C., 250° C. to 300° C. and also including a temperature of 275° C. to 300° C. at the inlet of the OCM reactor 10. In certain aspects, the hydrocarbon stream directed to the mixing device 504 has a temperature of less than or equal to 300° C., including a temperature of 15° C. to 300° C., 25° C. to 300° C., 50° C. to 300° C., 75° C. to 300° C., 100° C. to 300° C., 125° C. to 250° C., 150° C. to 225° C., 175° C. to 200° C., 15° C. to 250° C., 15° C. to 200° C., 15° C. to 150° C., 15° C. to 100° C., 15° C. to 75° C., and also including a temperature of 15° C. to 50° C. In certain aspects, the oxidant stream 518 directed to the mixing device 504 has a temperature of 0° C. to 250° C., including a temperature of 10° C. to 250° C., 20° C. to 250° C., 30° C. to 200° C., 30° C. to 150° C., 30° C. to 100° C., 30° C. to 50° C., 40° C. to 250° C., 100° C. to 250° C., 150° C. to 250° C., 200° C. to 250° C., and also including a temperature of 0° C. to 50° C.

The first stream 513 from the separations subsystem 503, which comprises CO and $H_2$ (i.e., byproducts of the OCM reaction) as well as $CH_4$, can provide the reactants (other than $O_2$) in the gas mixture feed 510 that contact the combustion catalyst and react/combust to generate a heated gas mixture having a temperature of at least 450° C., which heated gas mixture then contacts the OCM catalyst to initiate an OCM reaction and produce the OCM effluent 511. Accordingly, at least a portion of the $H_2$ and CO byproducts generated in the OCM reaction can be recycled to an OCM reactor of the OCM subsystem 501 as reactants that contact the combustion catalyst to autothermally heat the gas mixture feed 510 within the OCM reactor and thereby generate the heated gas mixture that contacts the OCM catalyst to initiate the OCM reaction and produce the $C_{2+}$ compounds.

Although not shown in FIG. 5, it is contemplated that an ignition component, as previously described, could be injected into an OCM reactor of the OCM subsystem 501. Furthermore, it is contemplated that a stream comprising $H_2$, CO, or both (e.g., syngas) could be added to the hydrocarbon stream that is directed to the mixing device 504 to form the gas mixture feed 510.

Figure 6:
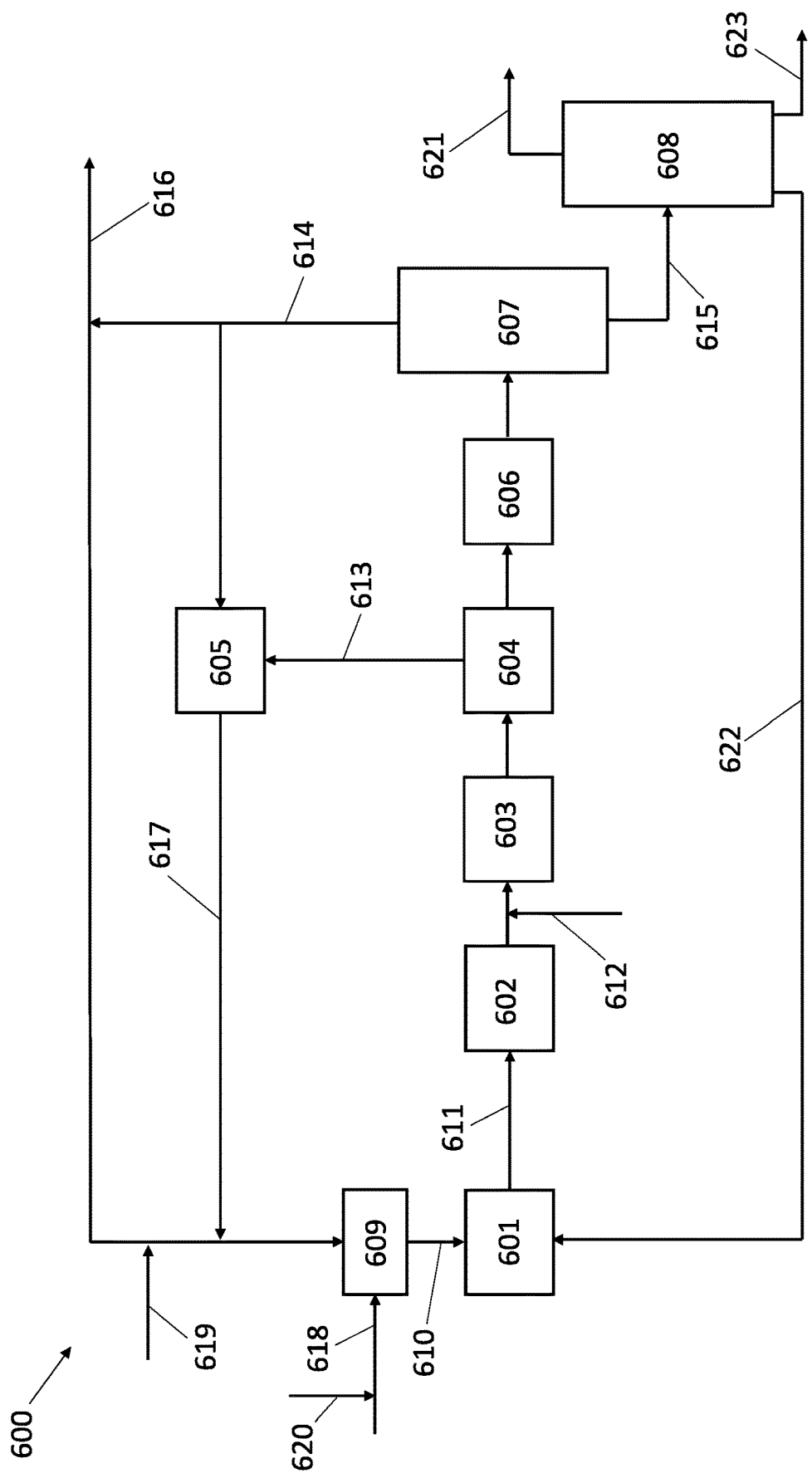
FIG. 6 illustrates a block flow diagram of an exemplary system for performing an oxidative coupling of methane reaction to produce $C_{2+}$ compounds in accordance with the present disclosure.

Referring now to FIG. 6, a block flow diagram of another implementation of a system 600 for performing an OCM reaction to produce $C_{2+}$ compounds, including ethylene ($C_2H_4$), in accordance with the present disclosure is shown. Similar to the system 500 illustrated in FIG. 5, the system 600 comprises an OCM subsystem 601 and a separations subsystem (not numbered). In addition, the system 600 includes a methanation subsystem 605. The OCM subsystem 601 is fluidly coupled to the separations subsystem and to the methanation system 605 and is configured to receive a gas mixture feed 610 having a temperature of less than or equal to 300° C. that comprises methane ($CH_4$), oxygen ($O_2$), hydrogen ($H_2$), and carbon monoxide (CO) and to generate an OCM effluent 611 comprising $C_{2+}$ compounds including $C_2H_4$ and $C_2H_6$ and non-$C_{2+}$ impurities comprising one or more of CO, $CO_2$, $H_2$, and $CH_4$.

In accordance with the methods and systems of the present disclosure, the OCM subsystem 601 includes an OCM reactor comprising a combustion catalyst and an OCM catalyst. In certain aspects, the OCM subsystem 601 includes an OCM reactor comprising a combustion catalyst and an OCM catalyst and a PBC unit. The OCM reactor and PBC unit of the OCM subsystem 601 may be configured the same as any one or more of the OCM reactors 10 and PBC units 60 previously described herein with reference to FIGS. 1-4.

As seen in FIG. 6, the gas mixture feed 610 is directed to the OCM subsystem 601 to generate an OCM effluent 611 comprising $C_{2+}$ compounds including $C_2H_4$ and $C_2H_6$ and non-$C_{2+}$ impurities comprising one or more of CO, $CO_2$, $H_2$, and $CH_4$. The OCM effluent 611 may be directed to one or more heat exchangers 602 to transfer heat from the OCM effluent 611 to a process stream and thereby cool the OCM effluent 611. In some aspects, the one or more heat exchangers may be a heat recovery steam generator (HRSG) that generates steam that may be used for heating, to generate power via a gas turbine, or for other processes.

With continued reference to FIG. 6, after passing through the one or more heat exchangers 602, the OCM effluent 611 may be directed to a process gas compressor 603 to increase the pressure of the OCM effluent 611 to a desired or suitable pressure such as at least 600 kPa (gauge), at least 800 kPa (gauge), at least 1,000 kPa (gauge), at least 1,200 kPa (gauge), at least 1,500 kPa (gauge), at least 1,750 kPa (gauge), or at least 2,000 kPa (gauge). In certain aspects of the methods and systems of the present disclosure, a natural gas stream 612 may be added to the OCM effluent 611 prior to entering the process gas compressor 603. The compressed OCM effluent 611 may be directed to a $CO_2$ removal unit 604 to remove $CO_2$ from the OCM effluent 611. At least a portion of the removed $CO_2$ may be directed to the methanation subsystem 605 via stream 613. In accordance with some aspects of the methods and systems of the present disclosure, all of the $CO_2$ removed by the $CO_2$ removal unit 604 is directed to the methanation subsystem 605 via stream 613. The $CO_2$ removal unit 604 may be configured the same as the $CO_2$ removal unit 502 described above. The substantially $CO_2$-free OCM effluent 611 may be directed to a process gas dryer 606 to remove $H_2O$ from the substantially $CO_2$-free OCM effluent 611. The process gas dryer 606 may be one or more molecular sieve dryers or separator vessels that remove $H_2O$ (either as a vapor or a liquid) from the substantially $CO_2$-free OCM effluent 611.

While FIG. 6 illustrates a $CO_2$ removal unit 604 positioned downstream of the OCM subsystem 601 and upstream of the separations subsystem, it is contemplated that $CO_2$ contained in the OCM effluent 611 may be removed via the separations subsystem, thereby eliminating the need for the $CO_2$ removal unit 604. Such an arrangement would be particularly suitable in systems where the separations subsystem is based on adsorption technology.

Still referring to FIG. 6, after exiting the process gas dryer 606, the substantially dry, substantially $CO_2$-free OCM effluent 611 may be directed to a separations subsystem that is downstream of and fluidly coupled to the OCM subsystem 601 and that comprises at least a demethanizer unit 607 and a $C_2$ purification unit 608. The demethanizer unit 607 is fluidly coupled to the methanation system 605 and to the $C_2$ purification unit 608, as illustrated in FIG. 6. The demethanizer unit 607 is configured to receive the OCM effluent 611, to separate the OCM effluent into a first stream 614 comprising CO, $H_2$, and $CH_4$ and a second stream 615 comprising $C_{2+}$ compounds including $C_2H_4$ and $C_2H_6$. At least a portion of the first stream 614 is recycled to the OCM subsystem 601 to facilitate generation of the gas mixture feed 510. In accordance with some aspects of the methods and systems of the present disclosure, at least a portion of the first stream 614 is directed from the demethanizer unit 607 to the methanation subsystem 605 to generate a methanation effluent 617 comprising $CH_4$. In accordance with some aspects of the methods and systems of the present disclosure, at least a portion of the first stream 614 is purged via line 616 to prevent the accumulation of inert components (e.g., $N_2$) in the system 600.

The methanation subsystem 605 can include one or more methanation reactors that contain a methanation catalyst (e.g., a nickel-based catalyst, a ruthenium-based catalyst) for carrying out a methanation reaction to produce $CH_4$. The typical operating conditions of a methanation reactor can be at a pressure of 100 kPa to 5,000 kPa and a temperature of 150° C. to 400° C. In the methanation subsystem 605, the carbon oxides (e.g., $CO_2$, CO, or both) from streams 613 and 614 react with $H_2$ (e.g., $H_2$ contained in stream 614) to produce a methanation effluent 617 comprising $CH_4$ via the following reactions: i) $CO_2 + 4\ H_2 \rightarrow CH_4 + 2\ H_2O$ and ii) $CO + 3\ H_2 \rightarrow CH_4 + H_2O$.

In accordance with certain aspects of the methods and systems of the present disclosure, the system 600 comprises a mixing device 609 fluidly coupled to the OCM subsystem 601, the separations subsystem (e.g., via demethanizer unit 607), and the methanation subsystem 605, as shown in FIG. 6. The mixing device 609 facilitates formation of the gas mixture feed 610 that is directed to the OCM subsystem 601. As seen in FIG. 6, the mixing device 609 receives an oxidant stream 518 comprising oxygen and a hydrocarbon stream that comprises at least a portion of the first stream 614 from the demethanizer unit 607 and the methanation effluent 617. In certain aspects of the methods and systems of the present disclosure, an optional methane or natural gas stream 619 can be added to the first stream 614 along with the methanation effluent 617 to form the hydrocarbon stream that is directed to the mixing device 609. In certain aspects of the methods and systems of the present disclosure, the oxidant stream 618 is provided by an air stream or an $O_2$ stream that is generated by an air separation unit. In certain aspects of the methods and systems of the present disclosure, the oxidant stream 618 further comprises steam, which may be injected or otherwise added into the oxidant stream 618 via line 620. The mixing device 609 may be any known device suitable for mixing together a first gas stream comprising hydrocarbons and a second gas stream comprising oxygen such as, for example, the mixing device described in U.S. Pat. No. 3,706,534. In certain aspects, the mixing device 609 comprises process piping or a mixing tee.

The gas mixture feed 610 has a temperature of less than or equal to 300° C. when exiting the mixing device 609 and entering an inlet of an OCM reactor of the OCM subsystem 601. In certain aspects, the gas mixture feed 610 has a temperature of 15° C. to 300° C. at an inlet of the OCM reactor 10, including a temperature of 50° C. to 300° C., 100° C. to 300° C., 100° C. to 250° C., 100° C. to 225° C., 100° C. to 200° C., 100° C. to 175° C., 100° C. to 150° C., 100° C. to 125° C., 125° C. to 300° C., 150° C. to 300° C., 175° C. to 300° C., 200° C. to 300° C., 225° C. to 300° C., 250° C. to 300° C. and also including a temperature of 275° C. to 300° C. at the inlet of the OCM reactor 10. In certain aspects, the hydrocarbon stream directed to the mixing device 609 has a temperature of less than or equal to 300° C., including a temperature of 15° C. to 300° C., 25° C. to 300° C., 50° C. to 300° C., 75° C. to 300° C., 100° C. to 300° C., 125° C. to 250° C., 150° C. to 225° C., 175° C. to 200° C., 15° C. to 250° C., 15° C. to 200° C., 15° C. to 150° C., 15° C. to 100° C., 15° C. to 75° C., and also including a temperature of 15° C. to 50° C. In certain aspects, the oxidant stream 618 directed to the mixing device 609 has a temperature of 0° C. to 250° C., including a temperature of 10° C. to 250° C., 20° C. to 250° C., 30° C. to 200° C., 30° C. to 150° C., 30° C. to 100° C., 30° C. to 50° C., 40° C. to 250° C., 100° C. to 250° C., 150° C. to 250° C., 200° C. to 250° C., and also including a temperature of 0° C. to 50° C.

The first stream 614 from the demethanizer unit 607, which comprises CO and $H_2$ (i.e., byproducts of the OCM reaction) as well as $CH_4$, can provide the reactants (other than $O_2$) in the gas mixture feed 610 that contact the combustion catalyst and react/combust to generate a heated gas mixture having a temperature of at least 450° C., which heated gas mixture then contacts the OCM catalyst to initiate an OCM reaction and produce the OCM effluent 611. Accordingly, at least a portion of the $H_2$ and CO byproducts generated in the OCM reaction can be recycled to an OCM reactor of the OCM subsystem 601 as reactants that contact the combustion catalyst to autothermally heat the gas mixture feed 610 within the OCM reactor and thereby generate the heated gas mixture that contacts the OCM catalyst to initiate the OCM reaction and produce the $C_{2+}$ compounds.

Although not shown in FIG. 6, it is contemplated that an ignition component, as previously described, could be injected into an OCM reactor of the OCM subsystem 601. Furthermore, it is contemplated that a stream comprising $H_2$, CO, or both (e.g., syngas) could be added to the hydrocarbon stream that is directed to the mixing device 609 to form the gas mixture feed 610.

With continued reference to FIG. 6, the second stream 615 comprising $C_{2+}$ compounds including $C_2H_4$ and $C_2H_6$ may be directed to the $C_2$ purification unit 608. The $C_2$ purification unit 608 is fluidly coupled to the OCM subsystem 601 and is configured to receive the second stream 615 and to separate the second stream 615 into at least a third stream 621 comprising $C_2H_4$ and a fourth stream 622 comprising $C_2H_6$. The third stream 621 comprising $C_2H_4$ may be collected or directed to a downstream process that utilizes $C_2H_4$ as a feedstock. As seen in FIG. 6, the fourth stream 622 comprising $C_2H_6$ may be recycled to the OCM subsystem 601 (e.g., to an OCM reactor or to a PBC unit) to produce additional $C_2H_4$ and $H_2$ by cracking the $C_2H_6$. In some aspects of the methods and systems of the present disclosure, the $C_2$ purification unit 608 may include a deethanizer unit (not shown) that is capable of separating $C_2$ compounds (e.g., ethane and ethylene) from $C_{3+}$ compounds (e.g., propane, propylene, butane, butene). Separated $C_{3+}$ compounds can leave the deethanizer unit along stream 623 and undergo additional downstream processing. The $C_2$ compounds from the deethanizer unit can be directed to a $C_2$ splitter (not shown), which can separate $C_2H_6$ from $C_2H_4$. The $C_2$ splitter can be a distillation column.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more (e.g., 1 to 6.1), and ending with a maximum value of 10 or less (e.g., 2.3 to 9.4, 3 to 8, 4 to 7), and finally to each number 1, 2, 3, 4, 5, 6, 7, 8, 9, and 10 contained within the range.

The methods and systems of the present disclosure can comprise, consist of, or consist essentially of the essential elements and limitations of the disclosure as described herein, as well as any additional or optional components or features described herein or otherwise known to be useful in hydrocarbon or petrochemical processing applications, including oxidative coupling of methane applications.

To the extent that the terms "include," "includes," or "including" are used in the specification or the claims, they are intended to be inclusive in a manner similar to the term "comprising" as that term is interpreted when employed as a transitional word in a claim. Furthermore, to the extent that the term "or" is employed (e.g., A or B), it is intended to mean "A or B or both A and B." When the Applicant intends to indicate "only A or B but not both," then the term "only A or B but not both" will be employed. Thus, use of the term "or" herein is the inclusive, and not the exclusive use. Furthermore, the phrase "at least one of A, B, and C" should be interpreted as "only A or only B or only C or any combinations thereof." In the present disclosure, the words "a" or "an" are to be taken to include both the singular and the plural. Conversely, any reference to plural items shall, where appropriate, include the singular.

In accordance with the present disclosure, it is possible to utilize the various inventive concepts in combination with one another. Additionally, any particular feature recited as relating to a particularly disclosed aspect of the methods and systems of the present disclosure should be interpreted as available for use with all disclosed aspects of the methods and systems of the present disclosure, unless incorporation of the particular feature would be contradictory to the express terms of the disclosed aspect. Additional advantages and modifications will be readily apparent to those skilled in the art. Therefore, the disclosure, in its broader aspects, is not limited to the specific details presented therein, the representative apparatus, or the illustrative examples shown and described. Accordingly, departures may be made from such details without departing from the spirit or scope of the general inventive concepts.

The scope of the general inventive concepts presented herein is not intended to be limited to the particular exemplary aspects shown and described herein. From the disclosure given, those skilled in the art will not only understand the general inventive concepts and their attendant advantages, but will also find apparent various changes and modifications to the devices, systems, and methods disclosed. It is sought, therefore, to cover all such changes and modifications as fall within the spirit and scope of the general inventive concepts, as described and/or claimed herein, and any equivalents thereof.

What is claimed is:

1. A method of performing an oxidative coupling of methane (OCM) reaction to produce $C_{2+}$ compounds, the method comprising:
   (a) introducing a gas mixture feed comprising methane ($CH_4$), oxygen ($O_2$), hydrogen ($H_2$), and carbon monoxide (CO) and having a temperature of less than or equal to 300° C. to an inlet of an OCM reactor, wherein the OCM reactor comprises a combustion catalyst and an OCM catalyst;
   (b) contacting the combustion catalyst with the gas mixture feed to combust at least a portion of the gas mixture feed and generate a heated gas mixture having a temperature of at least 450° C.; and
   (c) contacting the OCM catalyst with the heated gas mixture to initiate an OCM reaction and produce an OCM effluent comprising (i) $C_{2+}$ compounds including ethylene and ethane, and (ii) non-$C_{2+}$ impurities comprising one or more of CO, $CH_4$, $H_2$, and carbon dioxide ($CO_2$).

2. The method of claim 1, wherein the combustion catalyst comprises a metal, a metal oxide, or a mixed metal oxide, wherein the metal, the metal oxide, or the mixed metal oxide comprises at least one of platinum, chromium, copper, palladium, cobalt, iron, manganese, gold, cerium, bismuth, indium, molybdenum, rhodium, ruthenium, germanium, gadolinium, antimony, thallium, tellurium, lead, zinc, or tin.

3. The method of claim 1, wherein the gas mixture feed has a temperature of 15° C. to 250° C. at the inlet of the OCM reactor.

4. The method of claim 1, wherein the OCM reactor further comprises at least one ignition source, wherein the at least one ignition source promotes ignition of components of the gas mixture feed.

5. The method of claim 4, wherein the at least one ignition source is in contact with the combustion catalyst and comprises at least one of an electrically powered cartridge heater or a steam heated pipe.

6. The method of claim 4, wherein the at least one ignition source is positioned upstream of both the combustion catalyst and the OCM catalyst and comprises an injection of superheated steam at a temperature of 600° C. to 1,000° C.

7. The method of claim 1, wherein the OCM reaction has a selectivity for $C_{2+}$ compounds of at least 35%.

8. The method of claim 1, wherein the combustion catalyst preferentially combusts $H_2$, CO, or both over $CH_4$.

9. A method of performing an oxidative coupling of methane (OCM) reaction to produce $C_{2+}$ compounds, the method comprising:
(a) mixing an oxidant stream comprising oxygen ($O_2$) having a temperature of 0° C. to 50° C. with a hydrocarbon stream comprising methane ($CH_4$), carbon monoxide (CO), and hydrogen ($H_2$) having a temperature of less than or equal to 300° C. to form a gas mixture feed having a temperature of less than or equal to 300° C.;
(b) introducing the gas mixture feed to an inlet of an OCM reactor, wherein the OCM reactor comprises a combustion catalyst and an OCM catalyst;
(c) contacting the combustion catalyst with the gas mixture feed to combust at least a portion of gas mixture feed and generate a heated gas mixture having a temperature of at least 450° C.; and
(d) contacting the OCM catalyst with the heated gas mixture to initiate an OCM reaction and produce an OCM effluent comprising (i) $C_{2+}$ compounds including ethylene and ethane, and (ii) non-$C_{2+}$ impurities comprising one or more of CO, $CH_4$, $H_2$, and carbon dioxide ($CO_2$).

10. The method of claim 9, wherein the oxidant stream further comprises steam.

11. The method of claim 9, wherein the combustion catalyst comprises a metal, a metal oxide, or a mixed metal oxide, wherein the metal, the metal oxide, or the mixed metal oxide comprises at least one of platinum, chromium, copper, palladium, cobalt, iron, manganese, gold, cerium, bismuth, indium, molybdenum, rhodium, ruthenium, germanium, gadolinium, antimony, thallium, tellurium, lead, zinc, or tin.

12. The method of claim 9, wherein the gas mixture feed has a temperature of 15° C. to 250° C. at the inlet of the OCM reactor.

13. The method of claim 9, wherein the OCM reactor further comprises at least one ignition source, wherein the at least one ignition source promotes ignition of components of the gas mixture feed.

14. The method of claim 13, wherein the at least one ignition source is in contact with the combustion catalyst and comprises at least one of an electrically powered cartridge heater or a steam heated pipe.

15. The method of claim 13, wherein the at least one ignition source is positioned upstream of both the combustion catalyst and the OCM catalyst and comprises an injection of superheated steam at a temperature of 600° C. to 1,000° C.

16. The method of claim 9, wherein the OCM reaction has a selectivity for $C_{2+}$ compounds of at least 35%.

17. The method of claim 9, wherein the combustion catalyst preferentially combusts $H_2$, CO, or both over $CH_4$.

18. A system for performing an oxidative coupling of methane (OCM) reaction to produce $C_{2+}$ compounds, the system comprising:
an OCM reactor comprising a combustion catalyst and an OCM catalyst,
wherein the OCM reactor receives a gas mixture feed comprising methane ($CH_4$), oxygen ($O_2$), hydrogen ($H_2$), and carbon monoxide (CO) at a temperature of less than or equal to 300° C.,
wherein the combustion catalyst promotes combustion of at least a portion of the gas mixture feed to generate a heated gas mixture having a temperature of at least 450° C., and
wherein the OCM catalyst initiates an OCM reaction when contacted by the heated gas mixture and produces an OCM effluent comprising (i) $C_{2+}$ compounds including ethylene and ethane, and (ii) non-$C_{2+}$ impurities comprising one or more of CO, $CH_4$, $H_2$, and carbon dioxide ($CO_2$).

19. The system of claim 18, wherein the combustion catalyst comprises a metal, a metal oxide, or a mixed metal oxide, wherein the metal, the metal oxide, or the mixed metal oxide comprises at least one of platinum, chromium, copper, palladium, cobalt, iron, manganese, gold, cerium, bismuth, indium, molybdenum, rhodium, ruthenium, germanium, gadolinium, antimony, thallium, tellurium, lead, zinc, or tin.

20. The system of claim 18, wherein the OCM reactor further comprises at least one ignition source, wherein the at least one ignition source promotes ignition of components of the gas mixture feed.

21. The system of claim 20, wherein the at least one ignition source is in contact with the combustion catalyst and comprises at least one of an electrically powered cartridge heater or a steam heated pipe.

22. The system of claim 20, wherein the at least one ignition source is positioned upstream of both the combustion catalyst and the OCM catalyst and comprises a superheated steam injector that injects steam at a temperature of 600° C. to 1,000° C. into the OCM reactor.

23. The system of claim 18, wherein the combustion catalyst preferentially combusts $H_2$, CO, or both over $CH_4$.

* * * * *